United States Patent
Nishio et al.

(10) Patent No.: US 8,177,362 B2
(45) Date of Patent: May 15, 2012

(54) OPTICAL IMAGE MEASUREMENT DEVICE

(75) Inventors: Yutaka Nishio, Fussa (JP); Hiroaki Okada, Saitama (JP); Tsutomu Kikawa, Adachi-ku (JP); Kazuhiko Yumikake, Nerima-ku (JP)

(73) Assignee: Kabushiki Kaisha Topcon, Tokyo (JP)

( * ) Notice: Subject to any disclaimer, the term of this patent is extended or adjusted under 35 U.S.C. 154(b) by 281 days.

(21) Appl. No.: 12/450,881

(22) PCT Filed: Apr. 8, 2008

(86) PCT No.: PCT/JP2008/000901
§ 371 (c)(1),
(2), (4) Date: Oct. 16, 2009

(87) PCT Pub. No.: WO2008/129862
PCT Pub. Date: Oct. 30, 2008

(65) Prior Publication Data
US 2010/0110375 A1 May 6, 2010

(30) Foreign Application Priority Data
Apr. 18, 2007 (JP) .................. 2007-109027

(51) Int. Cl.
*A61B 3/14* (2006.01)
(52) U.S. Cl. ........................................ 351/206
(58) Field of Classification Search ............. 351/205, 351/206, 220, 221
See application file for complete search history.

(56) References Cited

U.S. PATENT DOCUMENTS

| | | |
|---|---|---|
| 2007/0070295 A1 | 3/2007 | Tsukada et al. |
| 2008/0068560 A1* | 3/2008 | Knighton et al. ............. 351/206 |

FOREIGN PATENT DOCUMENTS

| | | |
|---|---|---|
| EP | 1 775 545 A2 | 4/2007 |
| JP | 11-325849 | 11/1999 |
| JP | 2001-275979 | 10/2001 |
| JP | 2002-139421 | 5/2002 |
| JP | 2002-143088 | 5/2002 |
| JP | 2003-000543 | 1/2003 |
| JP | 2006-023476 | 1/2006 |

OTHER PUBLICATIONS

International Search Report dated May 13, 2008 issued in PCT/JP2008/000901.

* cited by examiner

*Primary Examiner* — Ricky Mack
*Assistant Examiner* — Mahidere Sahle
(74) *Attorney, Agent, or Firm* — Edwards Wildman Palmer LLP

(57) ABSTRACT

A device is an OCT device that splits a low-coherence light into a signal light and a reference light, detects an interference light obtained by superimposing the signal light propagated through an eye and the reference light propagated through a reference mirror, and forms an image of an fundus oculi. The device has a scan unit that scans the eye with the signal light. When a cross-section position is designated in an fundus oculi image, the device repetitively scans with the signal light along each cross-section position to repeatedly forms tomographic images at each cross-section position, thereby displaying a tomographic motion image at each cross-section position on a display. An operator can observe the tomographic motion image to designate the range and timing for measurement of a tomographic still image.

10 Claims, 10 Drawing Sheets

OPTICAL IMAGE MEASUREMENT DEVICE

TECHNICAL FIELD

The present invention relates to an optical image measurement device that scans a measurement object with a light beam and forms an image of the measurement object by using the reflected light.

BACKGROUND ART

In recent years, attention has been focused on an optical image measurement technique of forming an image showing the surface morphology or internal morphology of a measurement object by using a light beam emitted from a laser light source or the like. Because this optical image measurement technique does not have invasiveness to human bodies unlike an X-ray CT device, it is expected to employ this technique particularly in the medical field.

Patent Document 1 discloses an optical image measurement device configured in a manner that: a measuring arm scans an object by using a rotary deflection mirror (Galvano mirror); a reference mirror is disposed to a reference arm; at the outlet thereof, such an interferometer is used that the intensity of a light caused by interference of light fluxes from the measuring arm and the reference arm is analyzed by a spectrometer; and the reference arm is provided with a device gradually changing the light flux phase of the reference light in non-continuous values.

The optical image measurement device disclosed in Patent Document 1 uses a method of so-called "Fourier Domain OCT (Optical Coherence Tomography)." That is to say, the morphology of the measurement object in the depth direction (z-direction) is imaged by applying a beam of a low-coherence light to a measurement object, obtaining the spectrum intensity distribution of the reflected light, and subjecting the obtained distribution to Fourier transform.

Furthermore, the optical image measurement device described in Patent Document 1 is provided with a Galvano mirror scanning with a light beam (a signal light), thereby being capable of forming an image of a desired measurement region of a measurement object.

Because this optical image measurement device scans with the light beam only in one direction (x-direction) orthogonal to the z-direction, a formed image is a 2-dimensional tomographic image in the depth direction (z-direction) along the scanning direction of the light beam (the x-direction).

Further, Patent Document 2 discloses a technique of scanning with a signal light in both the horizontal and vertical directions to thereby form a plurality of 2-dimensional tomographic images in the horizontal direction and, based on the plurality of tomographic images, acquiring and imaging 3-dimensional tomographic information of a measurement range. A method for 3-dimensional imaging is, for example, a method of arranging and displaying a plurality of tomographic images in the vertical direction (referred to as stack data or the like), and a method of forming a 3-dimensional image by subjecting a plurality of tomographic images to a rendering process.

Further, Patent Document 3 discloses a configuration of using such an optical image measurement device in the ophthalmic field.

[Patent Document 1] Japanese Unexamined Patent Publication No. 11-325849
[Patent Document 2] Japanese Unexamined Patent Publication No. 2002-139421
[Patent Document 3] Japanese Unexamined Patent Publication No. 2003-543

DISCLOSURE OF THE INVENTION

Problem that the Invention is to Solve

Before acquiring an image with an optical image measurement device, it is necessary to set a site in a measurement object to acquire an image. For example, in the case of acquisition of an image of the fundus oculi, a measurement range is previously set so as to include an attention site such as the optic papilla, the macula and a lesion site.

Further, in the case of acquiring an image of a measurement object having a fine structure, it is required to precisely set a measurement range. However, it has been difficult to precisely set a measurement range with a conventional optical image measurement device.

Further, in the case of acquiring an image of a measurement object that changes with time, such as a living organism, it is desirable that it is possible to acquire an image at a desired timing while observing the condition of the measurement object. However, it has been difficult to acquire an image at a desired timing with a conventional optical image measurement device.

The present invention is for solving these problems, and an object of the present invention is to provide an optical image measurement device that allows highly accurate setting of a measurement range in a measurement object.

Another object of the present invention is to provide an optical image measurement device that allows acquisition of an image of a measurement object at a desired timing.

Means for Solving the Problem

In order to achieve the abovementioned objects, in a first aspect of the present invention, an optical image measurement device, which has: an interference-light generator configured to split a low-coherence light into a signal light and a reference light and superimpose the signal light propagated through an eye and the reference light propagated through a reference object to generate an interference light; a detector configured to detect the generated interference light; and a scanner configured to scan the eye with the signal light, and which forms an image of the eye based on a detection result from the detector, comprises: a designating part configured to designate one or more cross-section positions in the eye; a controller configured to control the scanner to execute a repetitive scan with a signal light along each of the designated cross-section positions; an image forming part configured to repetitively form a tomographic image at each of the cross-section positions, based on a detection result of an interference light based on the signal light with which the repetitive scan is executed; and a display configured to display a tomographic motion image at each of the cross-section positions, based on the repetitively formed tomographic image.

In a second aspect of the present invention, the optical image measurement device according to the first aspect further comprises a manipulation part, and is characterized in that: the controller is configured to, when the manipulation part is manipulated while the tomographic motion image is being displayed, control the scanner to execute a scan with a signal light along at least one cross-section position of the designated cross-section positions; and the image forming part is configured to form a tomographic still image at each of the at least one cross-section position, based on a detection result of an interference light based on the signal light with which the scan is executed.

In a third aspect of the present invention, the optical image measurement device according to the second aspect is characterized in that the controller is configured to set a number of scanning points in a scan with a signal light for acquisition of the tomographic motion image so as to be smaller than a number of scanning points in a scan with a signal light for acquisition of the tomographic still image.

In a fourth aspect of the present invention, the optical image measurement device according to the third aspect is characterized in that the controller is configured to, when scanning points of a signal light for acquisition of the tomographic still image are designated before measurement for acquisition of the tomographic motion image, set a smaller number of scanning points than the designated scanning points as scanning points for acquisition of the tomographic motion image.

In a fifth aspect of the present invention, the optical image measurement device according to the fourth aspect is characterized in that the controller is configured to, when two or more scanning lines with a plurality of scanning points arrayed as scanning points of the signal light are designated, set scanning lines for acquisition of the tomographic motion image based on the two or more scanning lines.

In a sixth aspect of the present invention, the optical image measurement device according to the fifth aspect is characterized in that the controller is configured to set two or more scanning lines acquired by removing one or more scanning points from the two or more scanning lines, as scanning lines for acquisition of the tomographic motion image.

In a seventh aspect of the present invention, the optical image measurement device according to the fifth aspect is characterized in that the controller is configured to set part of the two or more scanning lines as scanning lines for acquisition of the tomographic motion image.

In an eighth aspect of the present invention, the optical image measurement device according to the third aspect is characterized in that the controller is configured to, when scanning points of a signal light for acquisition of the tomographic motion image are designated before measurement for acquisition of the tomographic still image, set a larger number of scanning points than the designated scanning points, as scanning points for acquisition of the tomographic still image.

In a ninth aspect of the present invention, the optical image measurement device according to the second aspect further comprises an extracting part configured to analyze the tomographic motion image to extract a predetermined region of interest, and is characterized in that the controller is configured to set scanning lines of a signal light for acquisition of the tomographic still image so that a signal light is propagated through an attention site in the eye corresponding to the extracted region of interest.

In a tenth aspect of the present invention, the optical image measurement device according to the second aspect further comprises an extracting part configured to analyze the tomographic motion image and extract a predetermined region of interest, and is characterized in that the display is configured to display the extracted region of interest.

In an eleventh aspect of the present invention, the optical image measurement device according to the second aspect further comprises: an extracting part configured to analyze the tomographic motion image to extract a predetermined region of interest; and an informing part configured to inform when the region of interest is extracted.

In a twelfth aspect of the present invention, the optical image measurement device according to the first aspect further comprises a recording part configured to selectively record a frame of a tomographic motion image displayed on the display In a thirteenth aspect of the present invention, the optical image measurement device according to the first aspect is characterized in that the designating part includes an imaging part configured to take an image of the eye, and a designation manipulation part configured to designate a cross-section position on the taken image displayed on the display.

Effect of the Invention

According to the present invention, it is possible to repetitively scan with a signal light along each designated cross-section position, repetitively form a tomographic image at each cross-section position, and display a tomographic motion image.

Therefore, the operator can observe the tomographic motion image to designate a measurement range in a measurement object.

Consequently, it is possible to set a measurement range in a measurement object with high accuracy.

Further, since the operator can observe a tomographic motion image to designate a timing for measurement of a measurement object, it is possible to acquire an image of the measurement object at a desired timing.

BRIEF DESCRIPTION OF THE DRAWINGS

FIG. 7A shows an example of the scanning pattern of the signal light when the fundus oculi is seen from the incident side of the signal light into an eye. FIG. 7B shows an example of an arrangement pattern of scanning points on each scanning line.

Figure 1:
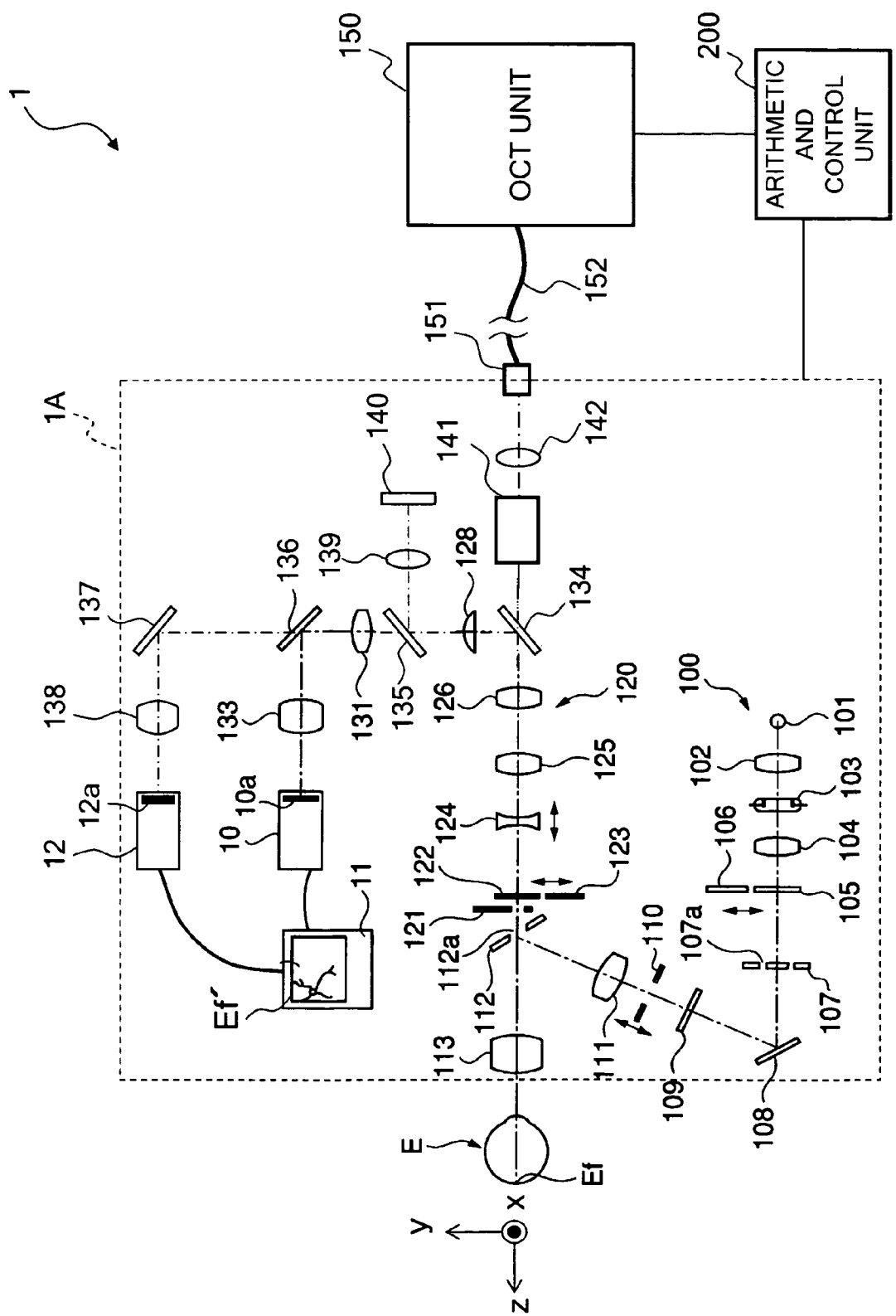
FIG. 1 is a schematic configuration diagram showing an example of the entire configuration in an embodiment of a fundus oculi observation device functioning as the optical image measurement device according to the present invention.

DESCRIPTION OF REFERENCE NUMERALS AND SYMBOLS 1 fundus oculi observation device (optical image measurement device)
1A retinal camera unit
140 LCD
141 scan unit
141A, 141B Galvano mirrors
150 OCT unit
160 low-coherence light source
162 optical coupler
174 reference mirror
180 spectrometer
184 CCD
200 arithmetic and control unit
204a control program
210 controller
211 main controller
212 storage
213 scan setting part
214 capture part
220 image forming part
230 image processor
231 image extracting part
240 user interface
240A display
240B manipulation part
241, 242 mirror drive mechanisms
Ri(i=1–m) scanning line
E eye
Ef fundus oculi

BEST MODE FOR CARRYING OUT THE INVENTION

An example of a preferred embodiment of an optical image measurement device according to the present invention will be described in detail with reference to the drawings.

An optical image measurement device according to the present invention is used in the ophthalmologic field. The optical image measurement device includes a function of displaying a motion image of tomographic images (a tomographic motion image) of an eye in real time. The tomographic motion image is a motion image acquired by repetitively measuring the same cross-section position at predetermined time intervals and displaying a plurality of tomographic images in chronological order at a predetermined frame rate.

[Device Configuration]

Figure 2:
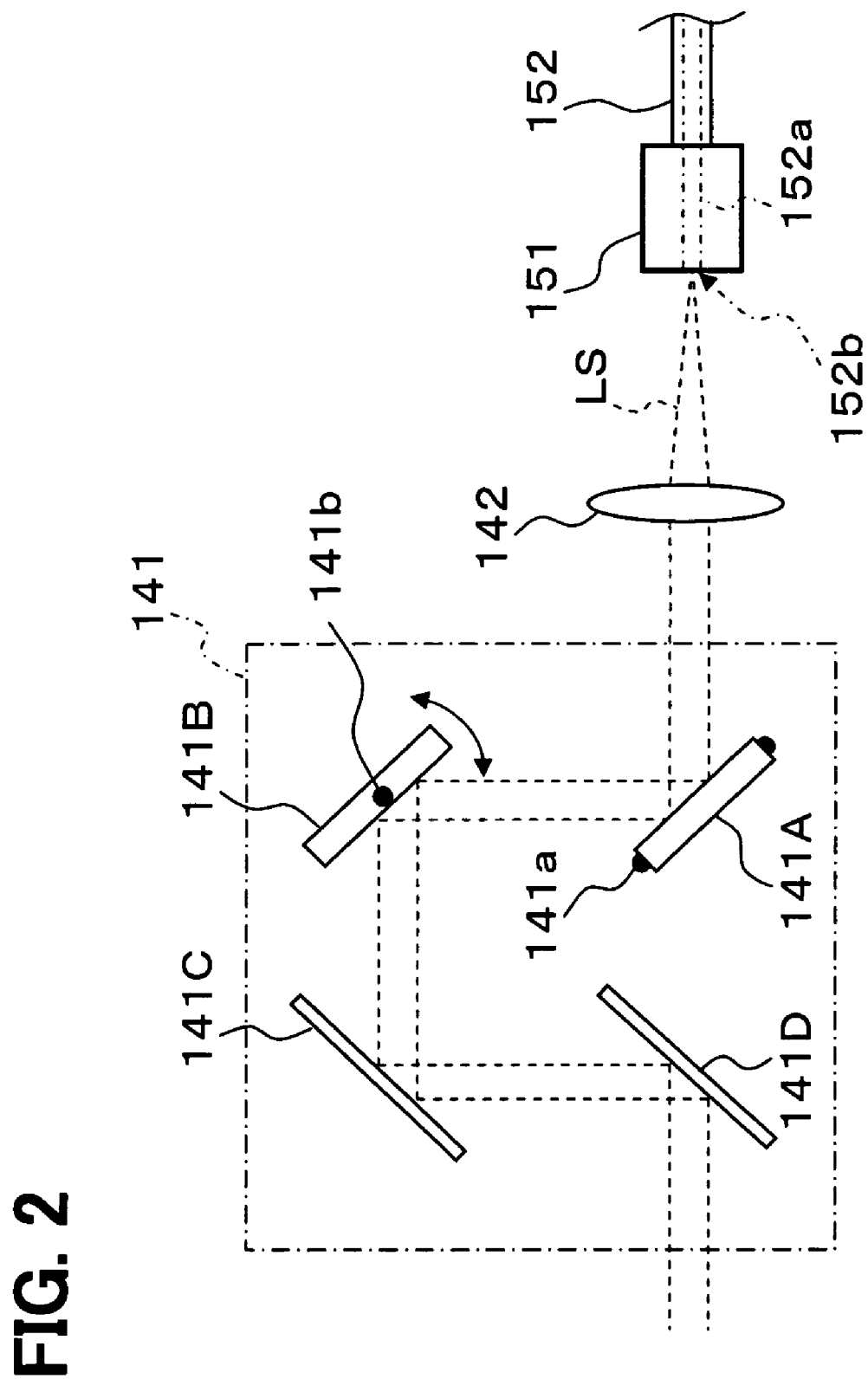
FIG. 2 is a schematic configuration diagram showing an example of the configuration of a scan unit installed in a retinal camera unit in the embodiment of the fundus oculi observation device functioning as the optical image measurement device according to the present invention.
Figure 3:
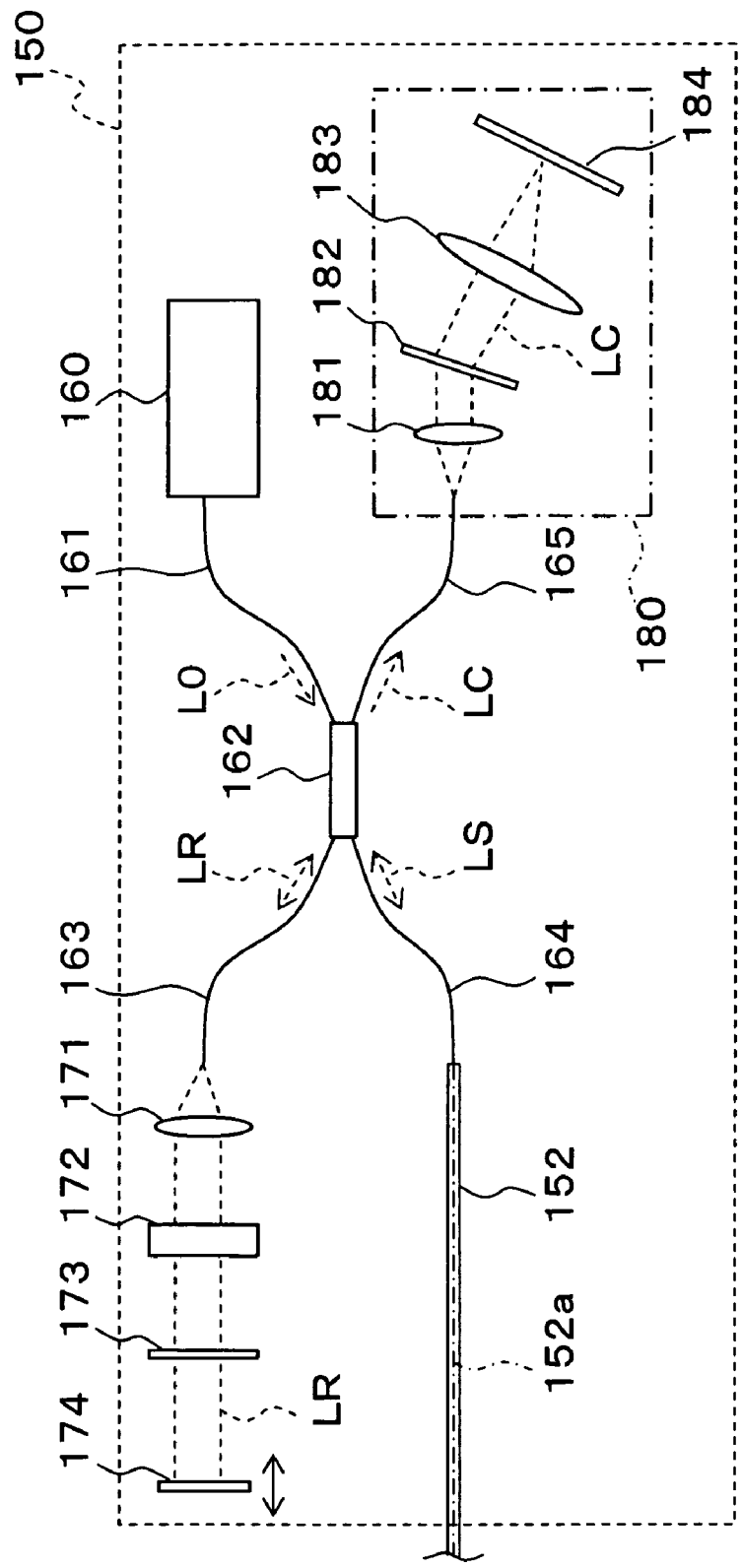
FIG. 3 is a schematic configuration diagram showing an example of the configuration of an OCT unit in the embodiment of the fundus oculi observation device functioning as the optical image measurement device according to the present invention.
Figure 4:
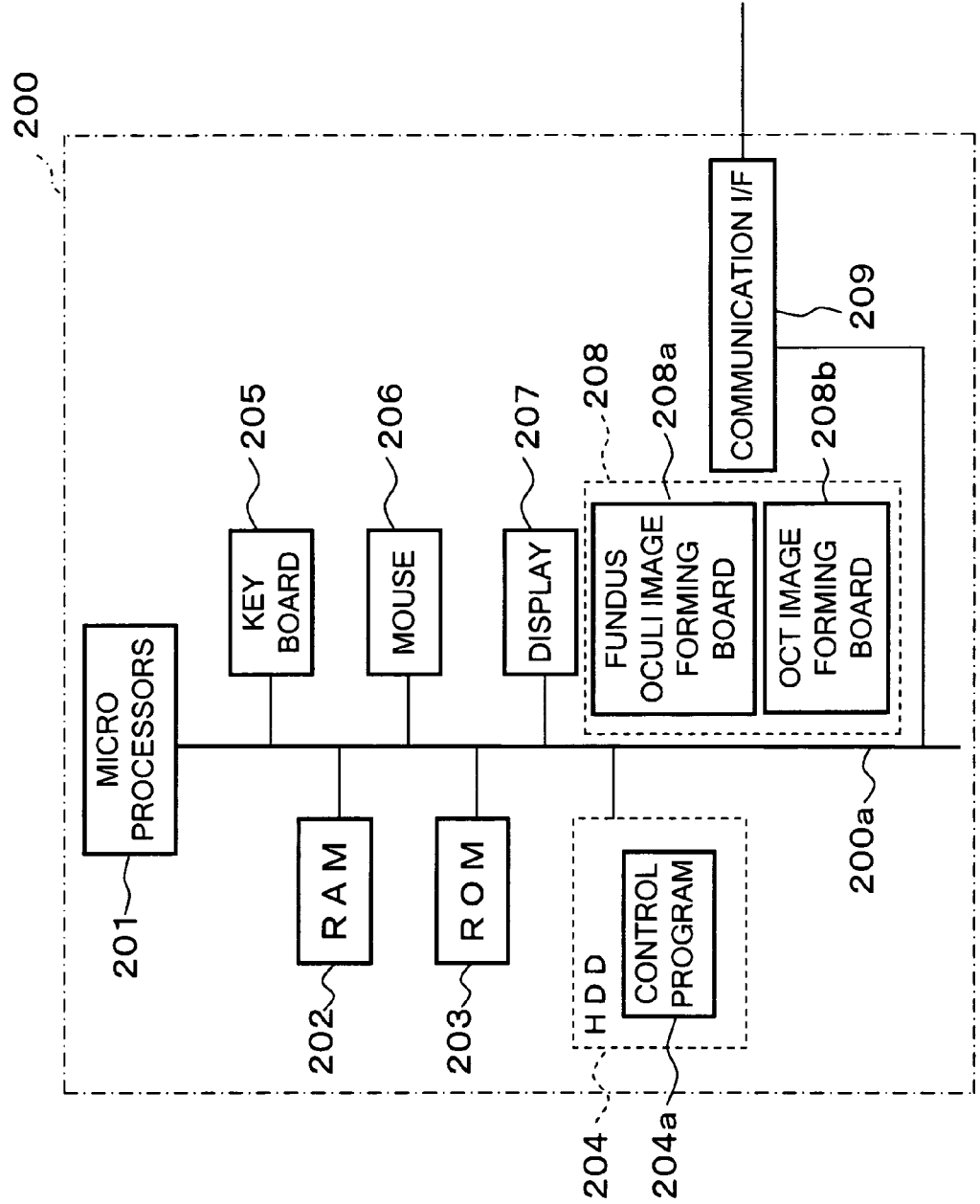
FIG. 4 is a schematic block diagram showing an example of the hardware configuration of an arithmetic and control unit in the embodiment of the fundus oculi observation device functioning as the optical image measurement device according to the present invention.
Figure 5:
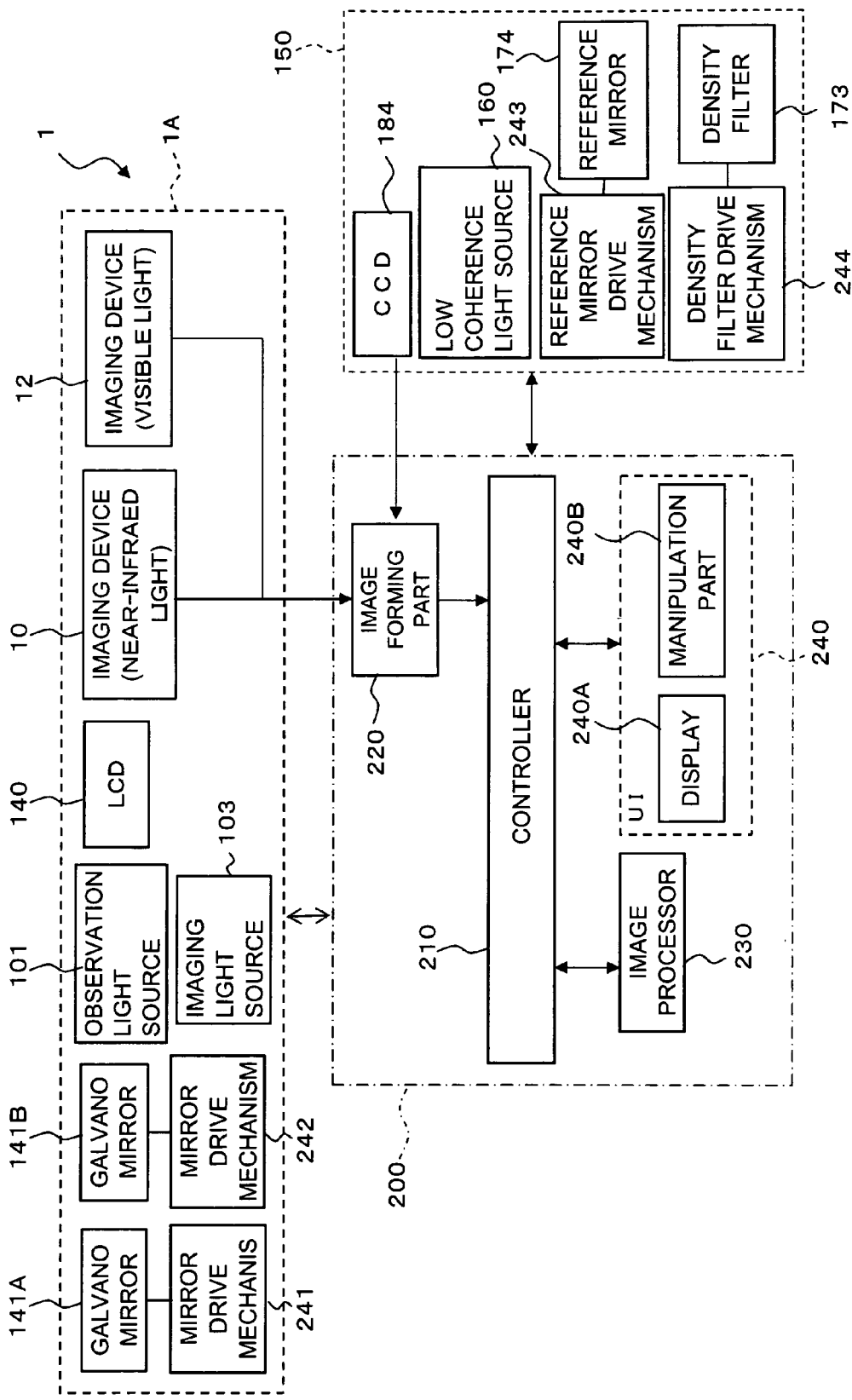
FIG. 5 is a schematic block diagram showing an example of the configuration of a control system in the embodiment of the fundus oculi observation device functioning as the optical image measurement device according to the present invention.
Figure 6:
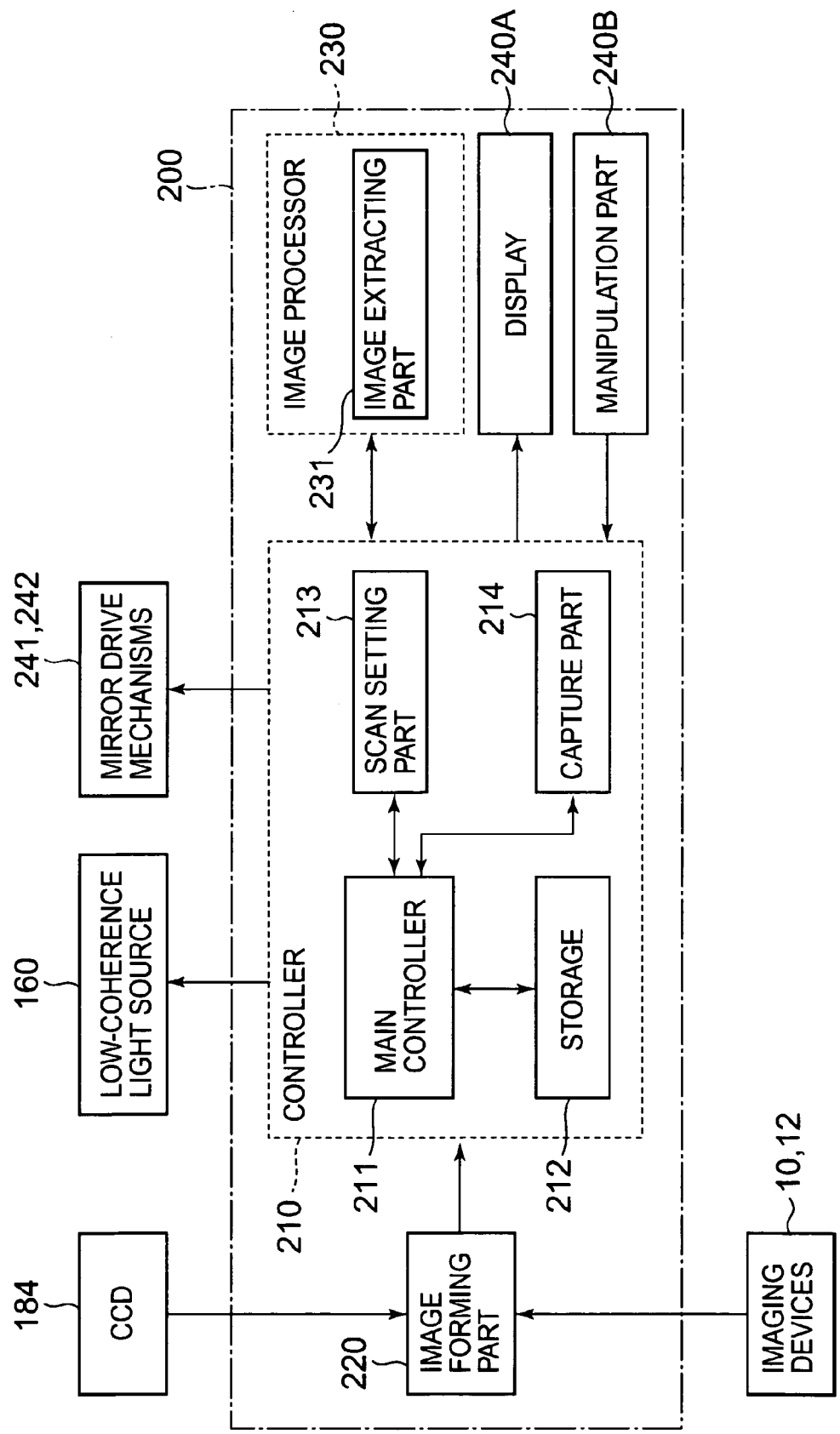
FIG. 6 is a schematic block diagram showing an example of the configuration of a control system in the embodiment of the fundus oculi observation device functioning as the optical image measurement device according to the present invention.

First, with reference to FIGS. 1 to 6, the configuration in an embodiment of the optical image measurement device according to the present invention will be described. FIG. 1 shows an example of the entire configuration of a fundus oculi observation device 1 having a function as the optical image measurement device according to the present invention. FIG. 2 shows an example of the configuration of a scan unit 141 in a retinal camera unit 1A. FIG. 3 shows an example of the configuration of an OCT unit 150. FIG. 4 shows an example of the hardware configuration of an arithmetic and control unit 200. FIGS. 5 and 6 show an example of the configuration of a control system of the fundus oculi observation device 1.

[Entire Configuration]

The fundus oculi observation device 1 includes the retinal camera unit 1A, the OCT unit 150, and the arithmetic and control unit 200 as shown in FIG. 1. The retinal camera unit 1A has almost the same optical system as a conventional retinal camera that captures a 2-dimensional image of the fundus oculi surface. The OCT unit 150 houses an optical system that functions as the optical image measurement device. The arithmetic and control unit 200 is provided with a computer that executes various kinds of arithmetic processes, control processes, etc.

To the OCT unit 150, one end of a connection line 152 is attached. A connector part 151 connecting the connection line 152 to the retinal camera unit 1A is attached to the other end of the connection line 152. A conductive optical fiber runs through inside the connection line 152. Thus, the OCT unit 150 and the retinal camera unit 1A are optically connected via the connection line 152.

[Configuration of Retinal Camera Unit]

The retinal camera unit 1A is used for taking a 2-dimensional image of the surface of the fundus oculi of an eye. The 2-dimensional image of the surface of the fundus oculi refers to a color image or monochrome image of the surface of the fundus oculi, a fluorescent image (e.g., a fluorescein angiography image and an indocyanine green fluorescent image), etc. As well as the conventional retinal camera, the retinal camera unit 1A is provided with an illumination optical system 100 that illuminates a fundus oculi Ef, and an imaging optical system 120 that guides the fundus oculi reflection light of the illumination light to an imaging device 10.

The imaging device 10 in the imaging optical system 120 detects an illumination light having a wavelength of a near-infrared region, the details of which will be described later. The imaging optical system 120 is also provided with an imaging device 12 detecting an illumination light having a wavelength of a visible region. The imaging optical system 120 guides a signal light coming from the OCT unit 150 to the fundus oculi Ef and guides the signal light propagated through the fundus oculi Ef to the OCT unit 150.

The illumination optical system 100 includes: an observation light source 101; a condenser lens 102; an imaging light source 103; a condenser lens 104; exciter filters 105 and 106; a ring transparent plate 107; a mirror 108; an LCD (Liquid Crystal Display) 109; an illumination diaphragm 110; a relay lens 111; an aperture mirror 112; and an objective lens 113.

The observation light source 101 outputs an illumination light having a wavelength of a visible region included in a range of about 400 nm to 700 nm, for example. The imaging light source 103 outputs an illumination light having a wavelength of a near-infrared region included in a range of about 700 nm to 800 nm, for example. The near-infrared light outputted from the imaging light source 103 is set so as to have a shorter wavelength than the light used by the OCT unit 150 (described later).

The imaging optical system 120 includes: the objective lens 113; the aperture mirror 112 (an aperture 112a thereof); an imaging diaphragm 121; barrier filters 122 and 123; a variable magnifying lens 124; a relay lens 125; an imaging lens 126; a dichroic mirror 134; a field lens 128; a half mirror 135; a relay lens 131; a dichroic mirror 136; an imaging lens 133; the imaging device 10 (image pick-up element 10a); a reflection mirror 137; an imaging lens 138; the imaging device 12 (image pick-up element 12a); a lens 139; and an LCD 140.

Further, the imaging optical system 120 includes: a dichroic mirror 134; a half mirror 135; a dichroic mirror 136; a reflection mirror 137; an imaging lens 138; a lens 139; and an LCD 140.

The dichroic mirror 134 is configured to reflect the fundus oculi reflection light (having a wavelength included in the range of about 400 nm to 800 nm) of the illumination light coming from the illumination optical system 100, and to transmit a signal light LS (having a wavelength included in the range of, for example, about 800 nm to 900 nm; described later) coming from the OCT unit 150.

The dichroic mirror 136 is configured to transmit the illumination light having a wavelength of the visible region coming from the illumination optical system 100 (a visible light having a wavelength of about 400 nm to 700 nm outputted from the observation light source 101), and to reflect the illumination light having a wavelength of the near-infrared region (a near-infrared light having a wavelength of about 700 nm to 800 nm outputted from the imaging light source 103).

The LCD 140 displays a fixation target (an internal fixation target) for fixing the eye E. A light from the LCD 140 is reflected by the half mirror 135 after being focused by the lens 139, and is reflected by the dichroic mirror 136 after propagated through the field lens 128. Furthermore, this light is propagated through the imaging lens 126, the relay lens 125, the variable magnifying lens 124, (the aperture 112a of) the aperture mirror 112, the objective lens 113, etc., and enters into the eye E. Consequently, the internal fixation target is projected on the fundus oculi Ef of the eye E.

The image pick-up element 10a is an image pick-up element such as a CCD (Charge Coupled Device) and a CMOS (Complementary Metal Oxide Semiconductor) installed in the imaging device 10 such as a TV camera, and particularly detects a light having a wavelength of the near-infrared region. In other words, the imaging device 10 is an infrared TV camera that detects a near-infrared light. The imaging device 10 outputs video signals as the result of detection of the near-infrared light.

A touch panel monitor 11 displays a 2-dimensional image of the surface of the fundus oculi Ef (a fundus oculi image Ef′), based on the video signals. The video signals are sent to the arithmetic and control unit 200, and the fundus oculi image is displayed on the display (described later).

For imaging the fundus oculi by the imaging device 10, for example, an illumination light outputted from the imaging light source 103 of the illumination optical system 100 and having a wavelength of the near-infrared region is used.

On the other hand, the image pick-up element 12a is an image pick-up element such as a CCD and a CMOS installed in the imaging device 12 such as a TV camera, and particularly detects a light having a wavelength of the visible region. That is to say, the imaging device 12 is a TV camera that detects a visible light. The imaging device 12 outputs video signals as the result of detection of the visible light.

The touch panel monitor 11 displays a 2-dimensional image of the surface of the fundus oculi Ef (the fundus oculi image Ef′), based on the video signals. The video signals are sent to the arithmetic and control unit 200, and the fundus oculi image is displayed on the display (described later).

For imaging the fundus oculi by the imaging device 12, for example, an illumination light outputted from the observation light source 101 of the illumination optical system 100 and having a wavelength of the visible region is used.

The retinal camera unit 1A is provided with a scan unit 141 and a lens 142. The scan unit 141 includes a component for scanning a projection position on the fundus oculi Ef with a light outputted from the OCT unit 150 (the signal light LS; described later).

The lens 142 makes the signal light LS guided from the OCT unit 150 through the connection line 152 enter into the scan unit 141 in the form of a parallel light flux. Moreover, the lens 142 focuses the fundus oculi reflection light of the signal light LS propagated through the scan unit 141.

FIG. 2 shows an example of the configuration of the scan unit 141. The scan unit 141 includes Galvano mirrors 141A and 141B, and reflection mirrors 141C and 141D.

The Galvano mirrors 141A and 141B are reflection mirrors disposed so as to be rotatable about rotary shafts 141a and 141b, respectively. The Galvano mirrors 141A and 141B are rotated about the rotary shafts 141a and 141b, respectively, by drive mechanisms described later (mirror drive mechanisms 241 and 242 shown in FIG. 5). Consequently, the reflection faces (the faces reflecting the signal light LS) of the Galvano mirrors 141A and 141B are turned around, respectively.

The rotary shafts 141a and 141b are arranged orthogonally to each other. In FIG. 2, the rotary shaft 141a of the Galvano mirror 141A is arranged in parallel to the paper face. On the other hand, the rotary shaft 141b of the Galvano mirror 141B is arranged in the orthogonal direction to the paper face.

That is to say, the Galvano mirror 141B is formed so as to be rotatable in the directions indicated by an arrow pointing in both directions in FIG. 2, whereas the Galvano mirror 141A is formed so as to be rotatable in the directions orthogonal to the arrow pointing in both the directions. Consequently, the Galvano mirrors 141A and 141B act so as to turn directions of reflecting the signal light LS into directions orthogonal to each other. As seen from FIGS. 1 and 2, a scan with the signal light LS is performed in the x-direction when the Galvano mirror 141A is rotated, and a scan with the signal light LS is performed in the y-direction when the Galvano mirror 141B is rotated.

The signal lights LS reflected by the Galvano mirrors 141A and 141B are reflected by reflection mirrors 141C and 141D, thereby traveling in the same direction as having entered into the Galvano mirror 141A.

An end face 152b of the optical fiber 152a inside the connection line 152 is arranged facing the lens 142. The signal light LS emitted from the end face 152b travels expanding its beam diameter toward the lens 142, and is made into a parallel light flux by the lens 142. On the contrary, the signal light LS propagated through the fundus oculi Ef is focused to the end face 152b by the lens 142, and enters into the optical fiber 152a.

[Configuration of OCT Unit]

Next, the configuration of the OCT unit 150 will be described with reference to FIG. 3. The OCT unit 150 is a device for forming a tomographic image of the fundus oculi based on optically obtained data (data detected by a CCD 184 described later).

The OCT unit 150 has almost the same optical system as a conventional optical image measurement device. That is to say, the OCT unit 150 splits a low-coherence light into a reference light and a signal light and superimposes the signal light propagated through an eye with the reference light propagated through a reference object, thereby generating and detecting an interference light. The result of this detection (a detection signal) is inputted to the arithmetic and control unit 200. The arithmetic and control unit 200 forms a tomographic image of the eye by analyzing the detection signal.

A low-coherence light source 160 is composed of a broadband light source, such as a super luminescent diode (SLD) and a light emitting diode (LED), which outputs a low-coherence light L0. The low-coherence light L0 is, for example, a light including a light with a wavelength of the near-infrared region and having a temporal coherence length of approximately several tens of micrometers.

The low-coherence light L0 has a longer wavelength than the illumination light of the retinal camera unit 1A (wavelength of about 400 nm to 800 nm), for example, a wavelength included in a range of about 800 nm to 900 nm.

The low-coherence light L0 outputted from the low-coherence light source 160 is guided to an optical coupler 162 through an optical fiber 161. The optical fiber 161 is composed of, for example, a single mode fiber or a PM (Polarization maintaining) fiber. The optical coupler 162 splits the low-coherence light L0 into a reference light LR and the signal light LS.

Although the optical coupler 162 acts as both a part (splitter) for splitting a light and a part (coupler) for superimposing lights, it will be herein referred to as an "optical coupler" idiomatically.

The reference light LR generated by the optical coupler 162 is guided by an optical fiber 163 composed of a single mode fiber or the like, and emitted from the end face of the fiber. Furthermore, the reference light LR is made into a parallel light flux by a collimator lens 171, propagated through a glass block 172 and a density filter 173, and reflected by a reference mirror 174. The reference mirror 174 is an example of the "reference object" of the present invention.

The reference light LR reflected by the reference mirror 174 is again propagated through the density filter 173 and the glass block 172, focused to the fiber end face of the optical fiber 163 by the collimator lens 171, and guided to the optical coupler 162 through the optical fiber 163.

The glass block 172 and the density filter 173 act as a delaying part for matching the optical path lengths (optical distances) of the reference light LR and the signal light LS, and also as a dispersion compensation part for matching the dispersion characteristics of the reference light LR and the signal light LS.

The density filter 173 also acts as a dark filter that reduces the amount of the reference light, and is composed of a rotating ND (neutral density) filter, for example. The density filter 173 acts so as to change the reduction amount of the reference light LR by being rotary driven by a drive mechanism including a drive unit such as a motor (a density-filter drive mechanism 244 described later; refer to FIG. 5). Consequently, it is possible to change the amount of the reference light LR contributing to generation of an interference light LC.

Further, the reference mirror 174 is configured to move in the traveling direction of the reference light LR (the direction of the arrow pointing both sides shown in FIG. 3). Thus, it is possible to ensure the optical path length of the reference light LR according to the axial length of the eye E, the working distance (the distance between the objective lens 113 and the eye E), etc. Moreover, it is possible to acquire an image of any depth position of the fundus oculi Ef, by moving the reference mirror 174. The reference mirror 174 is moved by a drive mechanism (a reference-mirror drive mechanism 243 described later; refer to FIG. 5) including a driver such as a motor.

On the other hand, the signal light LS generated by the optical coupler 162 is guided to the end of the connection line 152 through an optical fiber 164 composed of a single mode fiber or the like. The conductive optical fiber 152a runs inside the connection line 152.

The optical fiber 164 and the optical fiber 152a may be composed of one optical fiber, or may be integrally formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is guided through the inside of the connection line 152 and led to the retinal camera unit 1A.

Furthermore, the signal light LS is projected to the eye E through the lens 142, the scan unit 141, the dichroic mirror 134, the imaging lens 126, the relay lens 125, the variable magnifying lens 124, the imaging diaphragm 121, the aperture 112a of the aperture mirror 112 and the objective lens 113. The barrier filter 122 and 123 are retracted from the optical path in advance, respectively, when the signal light LS is projected to the eye E.

The signal light LS having entered into the eye E forms an image on the fundus oculi Ef and is then reflected. In this case, the signal light LS is not only reflected on the surface of the fundus oculi Ef, but also scattered at the refractive index boundary after reaching the deep area of the fundus oculi Ef. Therefore, the signal light LS propagated through the fundus oculi Ef contains information reflecting the morphology of the surface of the fundus oculi Ef and information reflecting the state of backscatter at the refractive index boundary of the deep area tissue of the fundus oculi Ef. This light may be simply referred to as the "fundus oculi reflection light of the signal light LS."

The fundus oculi reflection light of the signal light LS reversely travels along the abovementioned path within the retinal camera unit 1A, and is focused to the end face 152b of the optical fiber 152a. Then, the signal light LS enters into the OCT unit 150 through the optical fiber 152a, and returns to the optical coupler 162 through the optical fiber 164.

The optical coupler 162 superimposes the signal light LS returned through the eye E and the reference light LR reflected by the reference mirror 174, thereby generating the interference light LC.

The generated interference light LC is guided into a spectrometer 180 through an optical fiber 165 composed of a single mode fiber or the like.

Although a Michelson-type interferometer is adopted in this embodiment, it is possible to properly employ, for instance, a Mach Zender type, etc. and any type of interferometer.

The "interference-light generator" of the present invention includes, for example, an optical coupler 162, an optical member on the optical path of the signal light LS (i.e., an optical member placed between the optical coupler 162 and the eye E), and an optical member on the optical path of the reference light LR (i.e., an optical member placed between the optical coupler 162 and the reference mirror 174), and specifically, includes an interferometer equipped with the optical coupler 162, the optical fibers 163 and 164, and the reference mirror 174.

The spectrometer 180 includes a collimator lens 181, a diffraction grating 182, an image forming lens 183, and a CCD 184.

The diffraction grating 182 may be a transmission-type diffraction grating that transmits light, or may be a reflection-type diffraction grating that reflects light. Moreover, it is also possible to use, instead of the CCD 184, another photodetecting element such as a CMOS.

The interference light LC having entered into the spectrometer 180 is split (resolved into spectra) by the diffraction grating 182 after made into a parallel light flux by the collimator lens 181. The split interference light LC is formed into an image on the image pick-up face of the CCD 184 by the image forming lens 183. The CCD 184 detects the respective spectra of the split interference light LC and converts to electrical detection signals, and outputs the detection signals to the arithmetic and control unit 200. The CCD 184 is an example of the "detector" of the present invention.

[Configuration of Arithmetic and Control Unit]

The configuration of the arithmetic and control unit 200 will be described. The arithmetic and control unit 200 analyzes detection signals inputted from the CCD 184 of the OCT unit 150, and forms a tomographic image of the fundus oculi Ef. This analysis method is the same as the conventional Fourier Domain OCT method.

Further, the arithmetic and control unit 200 forms a 2-dimensional image showing the morphology of the surface of the fundus oculi Ef, based on the video signals outputted from the imaging devices 10 and 12 of the retinal camera unit 1A.

Furthermore, the arithmetic and control unit 200 controls each part of the retinal camera unit 1A and the OCT unit 150.

As control of the retinal camera unit 1A, the arithmetic and control unit 200 executes, for example: control of output of the illumination light by the observation light source 101 or the imaging light source 103; control of insertion/retraction operations of the exciter filters 105 and 106 or the barrier filters 122 and 123 to/from the optical path; control of the operation of a display device such as the LCD 140; control of movement of the illumination diaphragm 110 (control of the diaphragm value); control of the diaphragm value of the imaging diaphragm 121; and control of movement of the variable magnifying lens 124 (control of the magnification). Moreover, the arithmetic and control unit 200 executes control of the operation of the Galvano mirrors 141A and 141B.

On the other hand, as control of the OCT unit 150, the arithmetic and control unit 200 executes, for example: control of output of the low-coherence light L0 by the low-coherence light source 160; control of movement of the reference mirror 174; control of the rotary operation of the density filter 173 (the operation of changing the reduction amount of the reference light LR); and control of the accumulation time of the CCD 184.

The hardware configuration of the arithmetic and control unit 200 will be described with reference to FIG. 4.

The arithmetic and control unit 200 is provided with a similar hardware configuration to that of a conventional computer. To be specific, the arithmetic and control unit 200 includes: a microprocessor 201, a RAM 202, a ROM 203, a hard disk drive (HDD) 204, a keyboard 205, a mouse 206, a display 207, an image forming board 208, and a communication interface (I/F) 209. These parts are connected via a bus 200a.

The microprocessor 201 includes a CPU (Central Processing Unit), an MPU (Micro Processing Unit) or the like. The microprocessor 201 executes operations characteristic to this embodiment, by loading a control program 204a stored in the hard disk drive 204, onto the RAM 202.

Further, the microprocessor 201 executes control of each part of the device described above, various arithmetic processes, etc.

Further, the microprocessor 201 receives an operation signal from the keyboard 205 or the mouse 206, and executes control of each part of the device in response to the operation content. Furthermore, the microprocessor 201 executes control of a display process by the display 207, control of a transmission/reception process of data and signals by the communication interface 209.

The keyboard 205, the mouse 206 and the display 207 are used as user interfaces in the fundus oculi observation device 1. The keyboard 205 is used as, for example, a device for typing letters, figures, etc. The mouse 206 is used as a device for performing various input operations to the display screen of the display 207.

Further, the display 207 is a display device such as an LCD and a CRT (Cathode Ray Tube) display, and displays various images like an image of the fundus oculi Ef formed by the fundus oculi observation device 1, or displays various screens such as an operation screen and a set-up screen.

The user interface of the fundus oculi observation device 1 is not limited to the above configuration, and may include a track ball, a control lever, a touch panel type of LCD, a control panel for ophthalmology examinations, etc. As a user interface, it is possible to employ any configuration having a function of displaying and outputting information and a function of inputting information and operating the device.

The image forming board 208 is a dedicated electronic circuit for forming (image data of) images of the fundus oculi Ef. The image forming board 208 is provided with the fundus oculi image forming board 208a and an OCT image forming board 208b.

The fundus oculi image forming board 208a is a dedicated electronic circuit that forms image data of fundus oculi images based on the video signals from the imaging device 10 and the imaging device 12.

Further, the OCT image forming board 208b is a dedicated electronic circuit that forms image data of tomographic images of the fundus oculi Ef, based on the detection signals from the CCD 184 of the OCT unit 150.

By providing the image forming board 208, it is possible to increase the processing speed of a process for forming fundus oculi images and tomographic images.

The communication interface 209 sends control signals from the microprocessor 201, to the retinal camera unit 1A or the OCT unit 150. Moreover, the communication interface 209 receives video signals from the imaging devices 10 and 12 or detection signals from the CCD 184 of the OCT unit 150, and inputs the signals to the image forming board 208. At this moment, the communication interface 209 operates to input the video signals from the imaging devices 10 and 12, to the fundus oculi image forming board 208a, and input the detection signals from the CCD 184, to the OCT image forming board 208b.

Further, in a case where the arithmetic and control unit 200 is connected to a communication network such as a LAN (Local Area Network) and the Internet, it is possible to configure to be capable of data communication via the communication network, by providing the communication interface 209 with a network adapter like a LAN card or communication equipment like a modem. In this case, by mounting a server accommodating the control program 204a on the communication network, and also configuring the arithmetic and control unit 200 as a client terminal of the server, it is possible to operate the fundus oculi observation device 1.

[Configuration of Control System]

Next, the configuration of the control system of the fundus oculi observation device 1 will be described with reference to FIGS. 5 and 6.

(Controller)

The control system of the fundus oculi observation device 1 is configured mainly having a controller 210 of the arithmetic and control unit 200. The controller 210 includes the microprocessor 201, the RAM202, the ROM203, the hard disk drive 204 (the control program 204a), and the communication interface 209.

The controller 210 executes the aforementioned control by the microprocessor 201 that operates based on the control program 204a.

The controller 201 is provided with a main controller 211, a storage 212, a scan setting part 213, and a capture part 214. The controller 210 is an example of the "controller" according to the present invention.

The main controller 211 controls the mirror drive mechanisms 241 and 242 to control the positions of the Galvano mirrors 141A and 141B so as to scan the fundus oculi Ef with the signal light LS.

Further, the main controller 211 executes controls of the respective parts of the device, such as control of the low-coherence light source 160 to turn on/off, control of the CCD 184, control of the density-filter drive mechanism 244 to rotate the density filter 173, and control of the reference-mirror drive mechanism 243 to move the reference mirror 174 in the traveling direction of the reference light LR.

Further, the main controller 211 controls a display 240A of the user interface (UI) 240 to display two kinds of images taken by the fundus oculi observation device 1, i.e., the fundus oculi image Ef' and a tomographic image. These images may be displayed on the display 240A separately, or may be displayed side by side.

The storage 212 stores various kinds of data, such as image data formed by an image forming part 220. A process of writing the data into the storage 212 and a process of reading out the data from the storage 212 are executed by the main controller 211.

The scan setting part 213 sets information regarding a scan with the signal light LS. For example, the scan setting part 213 sets scanning points, scanning lines and scanning regions of the signal light LS. Details of this process will be described later.

The capture part 214 captures display information of an image, etc., displayed on the display 240A. For example, when a tomographic motion image of the fundus oculi Ef is displayed on the display 240A, the capture part 214 operates to selectively record a frame (still image) of the tomographic motion image. The capture part 214 is an example of the "recording part" according to the present invention.

(Image Forming Part)

The image forming part 220 forms image data of the fundus oculi image Ef' based on the video signals outputted from the imaging devices 10 and 12. The image forming part 220 also forms image data of the tomographic image of the fundus oculi Ef based on the detection signals outputted from the CCD 184 of the OCT unit 150. The image forming part 220 is an example of the "image forming part" according to the present invention.

The imaging forming part 220 includes the image forming board 208, the communication interface 209, etc. In this specification, "image" may be identified with "image data" corresponding thereto.

(Image Processor)

The image processor 230 applies various kinds of image processing and analysis processes to image data of images formed by the image forming part 220. For example, the image processor 230 executes various kinds of correction processes such as luminance correction and dispersion correction of the images.

Further, the image processor 230 applies an interpolation process of interpolating pixels between tomographic images formed by the image forming part 220 to the tomographic images, thereby forming image data of a 3-dimensional image of the fundus oculi Ef.

Image data of a 3-dimensional image is image data made by assigning pixel values to each of a plurality of voxels arranged 3-dimensionally, and is referred to as volume data, voxel data, or the like. In the case of displaying an image based on volume data, the image processor 230 executes a rendering process (such as volume rendering and MIP (Maximum Intensity Projection)) on this volume data, and forms image data of a pseudo 3-dimensional image seen from a specific view direction. On a display device such as the display 207, the pseudo 3-dimensional image based on the image data is displayed.

Further, the image processor 230 is also capable of forming stack data of a plurality of tomographic images. Stack data is image data that can be obtained by arranging a plurality of tomographic images acquired along a plurality of scanning lines based on the positional relationship of the scanning lines.

The image processor 230 is provided with an image extracting part 231. The image extracting part 231 analyzes a tomographic motion image and extracts a region of interest. A region of interest is an image region that represents an attention site in the fundus oculi Ef. The image extracting part 231 is an example of the "extracting part" of the present invention. An attention site in the fundus oculi Ef is the optic papilla, the macula, a lesion site, etc. In the case of acquisition of images of sites other than the fundus oculi, attention sites therein correspond to the sites.

A specific example of the process of extracting an attention site will be described. A tomographic motion image is composed of a plurality of frames. The image extracting part 231 extracts a region of interest from at least one frame.

In a case that a region of interest corresponds to a site such as the optic papilla and the macula, the region of interest can be extracted based on the shape of the site. For example, the optic papilla or the macula is concave to the back of the fundus oculi Ef (in the z-direction) when compared with its surrounding sites. The image extracting part 231 analyzes the pixel values of a frame, thereby specifying an image region corresponding to the surface of the fundus oculi Ef, i.e., the boundary between the retina and the vitreous body.

Then, the image extracting part 231 analyzes the shape of the specified image region, specifies a region that is concave in the z-direction, and extracts the region as a region of interest.

A case that a region of interest is a lesion site will be described below. Lesion sites in tomographic images include those identifiable from the shape such as retinal detachment, and those hard to identify from the shape such as tumors. The identifiable lesion sites can be extracted in a similar manner to the optic papilla, etc. On the other hand, the lesion sites hard to identify may be represented by pixel values (such as luminance) different from their surrounding sites. In this case, the image extracting part 231 can refer to the pixel value of each pixel of the frame to specify an image region corresponding to the lesion site and extract the region as a region of interest.

The image processor 230 operating as described above includes the microprocessor 201, the RAM 202, the ROM 203, the hard disk drive 204 (control program 204a), etc.

(User Interface)

The user interface (UI) 240 is provided with the display 240A and a manipulation part 240B. The display 240A is formed by a display device such as a display 207. The display 240A is an example of the "display" according to the present invention.

The manipulation part 240B is formed by input devices and manipulation devices such as a keyboard 205 and a mouse 206. The manipulation part 240B is an example of the "manipulation part" according to the present invention. The manipulation part 240B is also an example of the "designating part" for designating a cross-section position in the fundus oculi Ef, and is also an example of the "designation manipulation part" for designating a cross-section position on an fundus oculi image Ef'.

[Scan with Signal Light and Image Processing]

A scan with the signal light LS is performed by turning around the reflecting surfaces of the Galvano mirrors 141A and 141B of the scan unit 141 as described before. The controller 210 controls the mirror drive mechanisms 241 and 242, respectively, to turn around the reflecting surfaces of the Galvano mirrors 141A and 141B, respectively, thereby scanning the fundus oculi Ef with the signal light LS.

When the reflecting surface of the Galvano mirror 141A is turned around, a scan with the signal light LS in the horizontal direction (the x-direction in FIG. 1) is performed on the fundus oculi Ef. On the other hand, when the reflecting surface of the Galvano mirror 141B is turned around, a scan with the signal light LS in the vertical direction (the y-direction in FIG. 1) is performed on the fundus oculi Ef. Further, by turning around both the reflecting surfaces of the Galvano mirrors 141A and 141B simultaneously, it is possible to scan with the signal light LS in the composed direction of the x-direction and y-direction. That is to say, by controlling the two Galvano mirrors 141A and 141B, it is possible to scan with the signal light LS in any direction on the x-y plane.

Figure 7A:
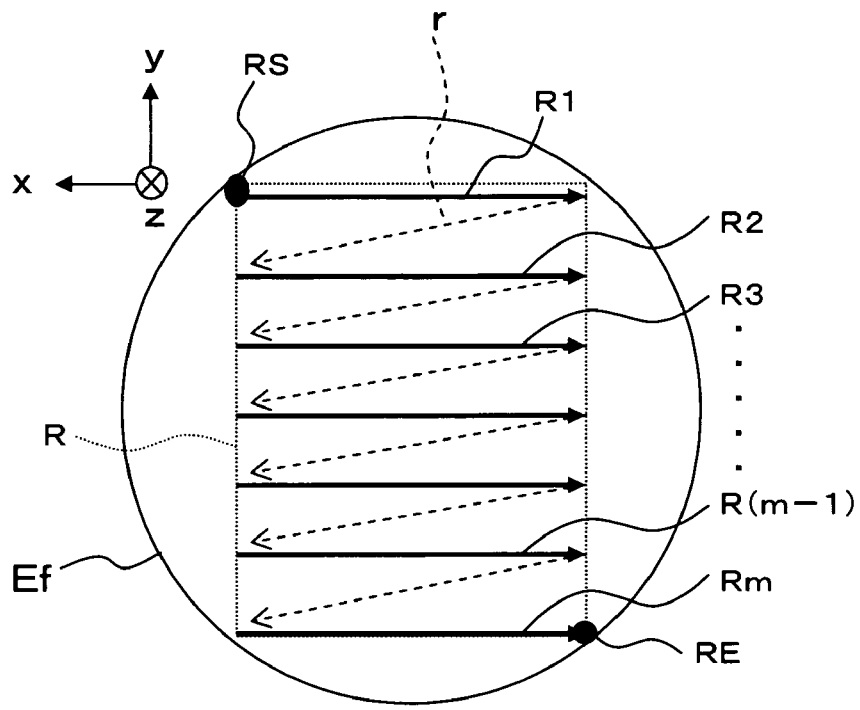
FIGS. 7A and 7B are schematic views showing an example of a scanning pattern of a signal light in the embodiment of the fundus oculi observation device functioning as the optical image measurement device according to the present invention.
Figure 7B:
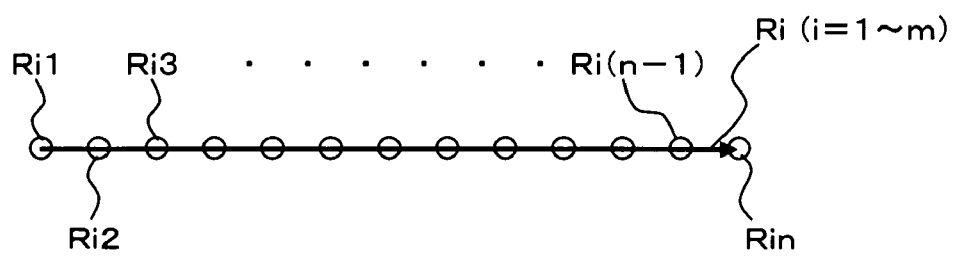

FIGS. 7A and 7B show an example of a scanning pattern of the signal light LS for forming an image of the fundus oculi Ef. FIG. 7A shows an example of the scanning pattern of the signal light LS when the fundus oculi Ef is seen from a direction in which the signal light LS enters the eye E (namely, seen from the −z side to the +z side in FIG. 1). Further, FIG. 7B shows an example of an arrangement pattern of scanning points (positions to perform image measurement) on each scanning line on the fundus oculi Ef.

As shown in FIG. 7A, a scan with the signal light LS is performed within a rectangular scanning region R set in advance.

Within the scanning region R, a plurality of (m lines of) scanning lines R1 to Rm are set in the x-direction. When a scan with the signal light LS is performed along each scanning line Ri (i=1 to m), a detection signal of the interference light LC is generated.

A direction of each scanning line Ri will be referred to as the "main scanning direction," and a direction orthogonal thereto will be referred to as the "sub-scanning direction." Accordingly, a scan with the signal light LS in the main scanning direction is performed by turning around the reflecting surface of the Galvano mirror 141A. A scan in the sub-scanning direction is performed by turning around the reflecting surface of the Galvano mirror 141B.

On each scanning line Ri, as shown in FIG. 7B, a plurality of (n pieces of) scanning points Ri1 to Rin are set in advance.

In order to execute the scan shown in FIGS. 7A and 7B, the controller 210 firstly controls the Galvano mirrors 141A and 141B to set the entering target of the signal light LS into the fundus oculi Ef to a scan start position RS (a scanning point R11) on the first scanning line R1. Subsequently, the controller 210 controls the low-coherence light source 160 to flush the low-coherence light L0, thereby making the signal light LS enter the scan start position RS.

The CCD 184 receives the interference light LC based on the fundus oculi reflection light of the signal light LS at the scan start position RS, and outputs the detection signal to the controller 210.

Next, the controller 210 controls the Galvano mirror 141A to scan with the signal light LS in the main scanning direction and set the entering target thereof to a scanning point R12, and causes the low-coherence light L0 to flush to make the signal light LS enter a scanning point R12. The CCD 184 receives the interference light LC based on the fundus oculi reflection light of this signal light LS at the scanning point R12, and outputs the detection signal to the controller 210.

In the same way, the controller 210 makes the low-coherence light L0 flush at each scanning point while moving the entering target of the signal light LS from a scanning point R13 to R14, - - - , R1 (n−1) and R1n in order, thereby obtaining a detection signal outputted from the CCD 184 in response to the interference light LC for each scanning point.

When the measurement at the last scanning point R1n of the first scanning line R1 ends, the controller 210 controls the Galvano mirrors 141A and 141B simultaneously to move the entering target of the signal light LS to a first scanning point R21 of a second scanning line R2 along a line switching scan r. Then, by conducting the aforementioned measurement for each scanning point R2j (j=1 to n) of this second scanning line R2, a detection signal corresponding to each scanning point R2j is obtained.

In the same way, the measurement is performed for each of a third scanning line R3, - - - , an m−1th scanning line R(m−1) and an mth scanning line Rm, whereby a detection signal corresponding to each scanning point is acquired. Symbol RE on the scanning line Rm is a scan end position corresponding to a scanning point Rmn.

As a result, the controller 210 obtains m×n pieces of detection signals corresponding to m×n pieces of scanning points Rij (i=1 to m, j=1 to n) within the scanning region R. Hereinafter, a detection signal corresponding to the scanning point Rij may be represented by Dij.

Interlocking control of the movement of the scanning point and the emission of the low-coherence light L0 as described above can be implemented by synchronizing a transmission timing of a control signal to the mirror drive mechanisms 241 and 242 and a transmission timing of a control signal to the low-coherence light source 160.

As described above, when making the respective Galvano mirrors 141A and 141B operate, the controller 210 stores the position of the scanning line Ri and the position of the scanning point Rij (coordinates on the x-y coordinate system) as information representing the content of the operation. This stored content (the scan position information) is used in an image forming process as conventional.

Next, an example of image processing in the case of a scan with the signal light LS shown in FIGS. 7A and 7B will be described.

The image forming part 220 forms tomographic images of the fundus oculi Ef along each scanning line Ri (the main scanning direction). Further, the image processor 230 forms a 3-dimensional image of the fundus oculi Ef based on the tomographic images formed by the image forming part 220.

A process of forming tomographic images by the image forming part 220 includes a 2-step arithmetic process as conventional.

In the first step of the arithmetic process, based on the detection signal Dij corresponding to each scanning point Rij, an image in the depth direction (the z-direction in FIG. 1) of the fundus oculi Ef at the scanning point Rij is formed.

Figure 8:
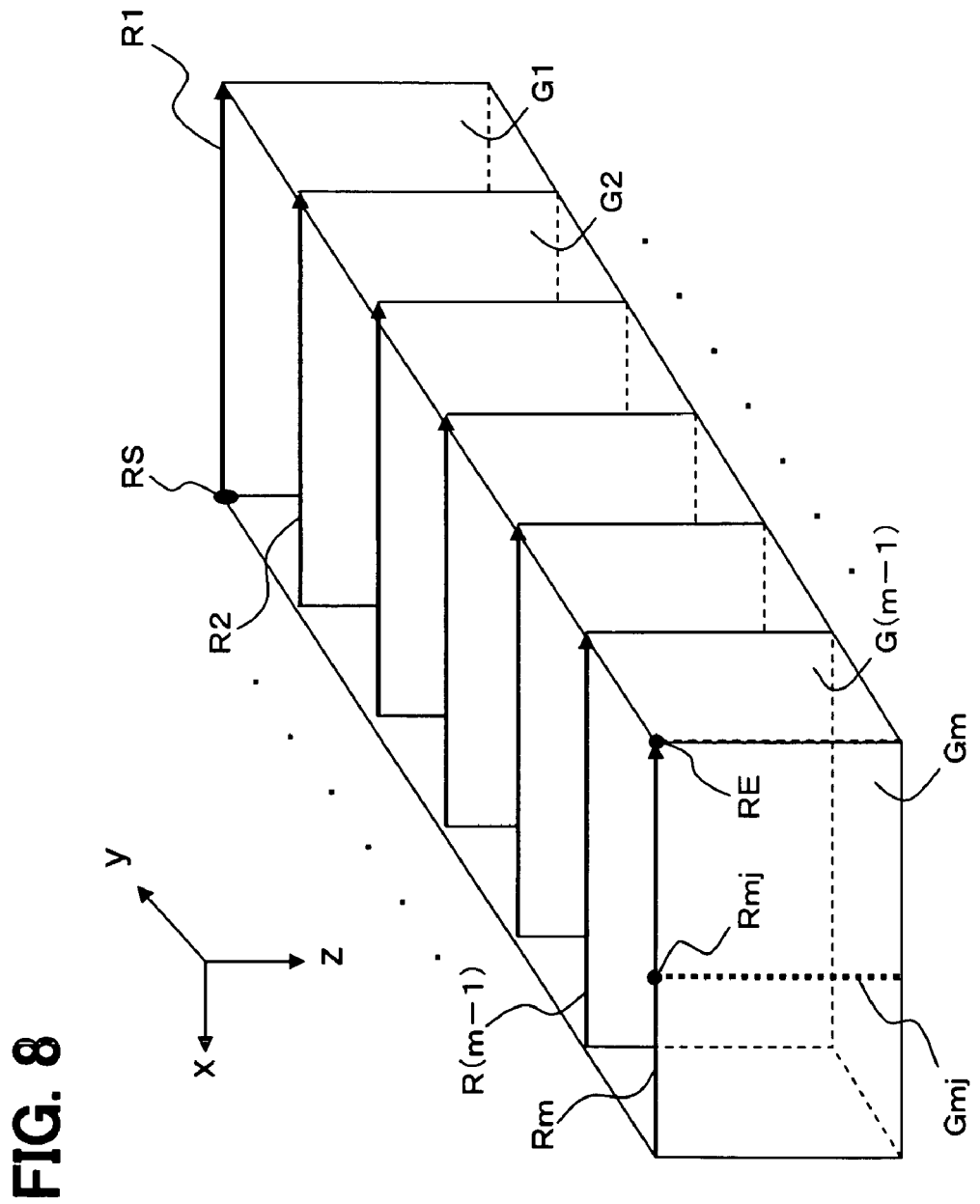
FIG. 8 is a schematic view showing an example of the scanning pattern of the signal light and a pattern of a tomographic image formed along each scanning line in the embodiment of the fundus oculi observation device functioning as the optical image measurement device according to the present invention.

FIG. 8 shows a pattern of tomographic images formed by the image forming part 220. In the second step of the arithmetic process, for each scanning line Ri, based on the images of the depth direction at the n pieces of scanning points Ri1 to Rin, a tomographic image Gi of the fundus oculi Ef along the scanning line Ri is formed. At this moment, the image forming part 220 determines the arrangement and interval of the scanning points Ri1 to Rin by referring to the positional information (scan position information described before) of the scanning points Ri1 to Rin, and forms this scanning line Ri.

Through the above process, it is possible to obtain m pieces of tomographic images G1 to Gm at different positions in the sub-scanning direction (y-direction).

Next, a process of forming a 3-dimensional image of the fundus oculi Ef by the image processor 230 will be described. A 3-dimensional image of the fundus oculi Ef is formed based on the m pieces of tomographic images obtained through the abovementioned arithmetic process. The image processor 230 forms a 3-dimensional image of the fundus oculi Ef, for example, by performing a known interpolating process of interpolating an image between the adjacent tomographic images Gi and G (i+1).

In this case, the image processor 230 determines the arrangement and interval of the scanning lines Ri by referring to the positional information of the scanning lines Ri, thereby forming a 3-dimensional image. For this 3-dimensional image, 3-dimensional coordinates (x, y, z) are set, based on the positional information of each scanning point Rij (the aforementioned scan position information) and the z coordinate in an image of the depth direction.

Further, based on this 3-dimensional image, the image processor 230 can form a tomographic image of the fundus oculi Ef at a cross section in any direction other than the main scanning direction (x-direction). When the cross section is designated, the image processor 230 specifies the position of each scanning point (and/or an interpolated image of the depth direction) on this designated cross section, extracts an image of the depth direction at each of the specified positions (and/or an interpolated depth-direction image) from the 3-dimensional image, and arranges the plurality of extracted images of the depth direction, thereby forming a tomographic image of the fundus oculi Ef at the designated cross section.

An image Gmj shown in FIG. 8 represents an image in the depth direction (z-direction) at the scanning point Rmj on the scanning line Rm. In the same way, an image in the depth direction at each scanning point Rij on the scanning line Ri formed in the aforementioned first-step arithmetic process is represented as the "image Gij."

Since the scanning pattern of the signal light LS shown in FIGS. 7A and B allows formation of a 3-dimensional image, this pattern shall be referred to as a "3-dimensional scan." Scanning patterns other than the 3-dimensional scan will be described below. First, a "horizontal scan" is a scan with the signal light LS along a scanning line extending in the main scanning direction (x-direction). Similarly, a "vertical scan" is a scan with the signal light LS along a scanning line extending in the sub-scanning direction (y-direction).

Furthermore, a "cross scan" can be executed by scanning with the signal light LS in the cruciform manner by combination of one scanning line extending in the main scanning direction and one scanning line extending in the sub-scanning direction. Moreover, a "radial scan" centered at a specific position can be executed by scanning with the signal light LS along radial scan lines by combination of a plurality of linear scanning lines passing the specific position in different directions.

Besides, a "circular scan" is a scan with the signal light LS along a circular scan line. The circular scan can be implemented by simultaneously controlling both the Galvano mirrors 141A and 141B.

Moreover, a "concentric scan" can be executed by combining a plurality of circular scans with different diameters. Furthermore, a "helical scan" can be executed by simultaneously controlling both the Galvano mirrors 141A and 141B and scanning with the signal light LS along a helical scan line.

The scanning patterns of the signal light LS are not limited to those described above. The storage 212 previously stores various scanning patterns, and the main controller 211 presents these scanning patterns on the display 240A in a selectable manner. The operator can select a desired scanning pattern by, for example, using the manipulation part 240B.

[Usage Pattern]

Figure 9:
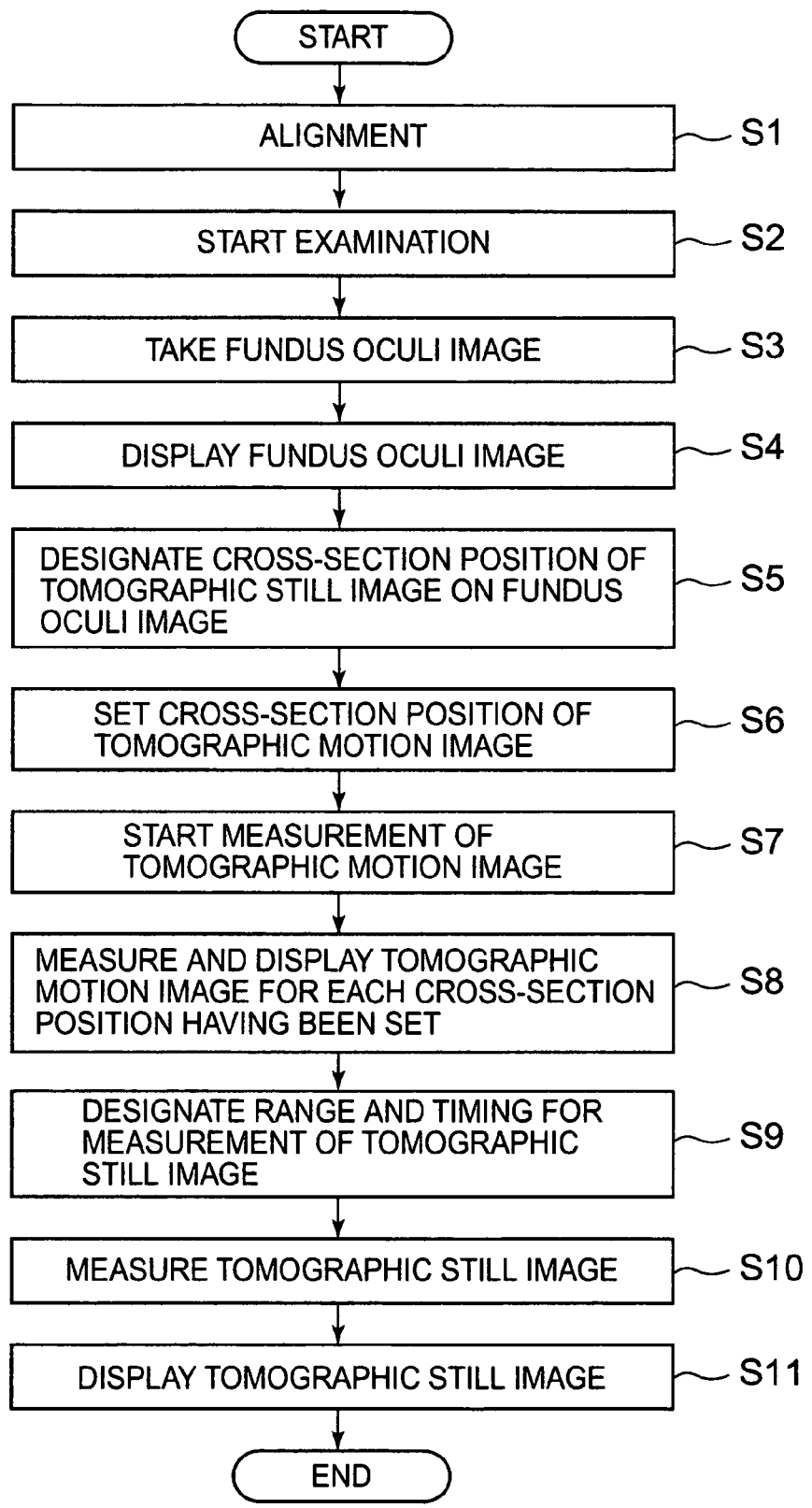
FIG. 9 is a flowchart showing an example of a usage pattern of the embodiment of the fundus oculi observation device functioning as the optical image measurement device according to the present invention.

A usage pattern of the fundus oculi observation device 1 will be described. A flowchart of FIG. 9 shows an example of the usage pattern of the fundus oculi observation device 1.

First, the eye E is positioned at a specific measurement position (a position facing the objective lens 113), and alignment with the eye E is performed (S1). After the alignment is completed, the operator manipulates the manipulation part 240B to require start (S2). The main controller 211 controls the LCD 140 as necessary to present an internal fixation target on the eye E.

In response to this request, the main controller 211 controls the observation light source 101 and the imaging device 12 (or the imaging light source 103 and the imaging device 10) to take the fundus oculi image Ef' of the fundus oculi Ef (S3) and controls the display 240A to display the fundus oculi image Ef' having been taken (S4).

The operator manipulates the manipulation part 240B to designate a cross-section position on the displayed fundus oculi image Ef' (S5). The cross-section position to be designated is a measurement position in a tomographic still image of the fundus oculi Ef. The tomographic still image is a tomographic image that is referred to in diagnosis of the fundus oculi Ef. On the other hand, the aforementioned tomographic motion image is a tomographic image that is utilized for setting the condition for measurement (e.g., a measurement position and resolution) of a tomographic still image.

In step 5, the operator can designate a cross-section position, in accordance with the attention site of the fundus oculi Ef, an observation method, etc. For example, when it is desired to observe a 3-dimensional image of the attention site of the fundus oculi Ef, it is possible to designate the 3-dimensional scan. When it is desired to observe a cross section passing through the attention site, it is possible to designate a cross-section position corresponding to the horizontal scan, vertical scan, cross scan, or radial scan. When it is desired to observe the condition of the surroundings of a certain attention point (e.g., the fovea centralis and the central papilla) in the fundus oculi, it is possible to designate a cross-section position corresponding to the circular scan, concentric scan, or helical scan. It is possible to apply the concentric scan and the helical scan to formation of a 3-dimensional image by setting the interval between the scanning lines to be small.

In step 5, instead of setting a cross-section position, the number of scanning lines or the scanning pattern may be designated.

It is also possible to set various conditions related to a scan with the signal light LS, such as intervals of scanning lines and intervals of scanning points, together with the cross-section position, etc. The designation of a cross-section position for image formation is synonymous with determination of a scanning point to which the signal light LS is applied as shown in FIG. 7.

When a cross-section position for measurement of the tomographic still image is designated, the scan setting part 213 sets a cross-section position for acquisition of a tomographic motion image of the fundus oculi Ef (S6).

A specific example of step 6 will be described below. The scan setting part 213 sets the number of scanning points for measurement of the tomographic motion image so as to be smaller than the number of scanning points for measurement of the tomographic still image.

For example, the scan setting part 213 sets the scanning points for measurement of the tomographic motion image by thinning out the scanning points for measurement of the tomographic still image.

Further, when two or more cross-section positions (scanning lines) are designated in step 5, the scan setting part 213 can set a smaller number of scanning lines than those for measurement of the tomographic motion image. For example, when the radial scan is designated for measurement of the tomographic still image, it is possible to set the horizontal scan, vertical scan, or cross scan. In this case, the central position for scan is the same.

The cross-section position for measurement of the tomographic still image and the cross-section position for measurement of the tomographic motion image do not need to have a relation that one includes the other. For example, it is possible to apply the cross scan as the former and apply the 3-dimensional scan as the latter.

The operator manipulates the manipulation part 240B to request measurement of the tomographic motion image (S7). In response to this request, the main controller 211 controls the low-coherence light source 160 and the mirror drive mechanisms 241 and 242 to repetitively scan with the signal light LS along the respective cross-section positions set in step 6. The CCD 184 detects the interference light LC corresponding to each scanning point and outputs a detection signal. The image forming part 220 repetitively forms a tomographic image at each of the cross-section positions based on the detection signal outputted from the CCD 184.

Consequently, at each of the cross-section positions, tomographic images are obtained at predetermined time intervals.

The main controller 211 controls the display 240A to display, at a predetermined frame rate, the tomographic images repetitively formed at each of the cross-section positions, thereby displaying a tomographic motion image at each of the cross-section positions (S8).

A specific example of step 8 will be described below. In this example, in the 3-dimensional scan shown in FIGS. 7A and 7B, a scan with the signal light LS is executed along the scanning lines with odd numbers, R1, R3, R5, etc. (the scanning lines with even numbers R2, R4, etc., are omitted). The main controller 211 controls to scan with the signal light LS along the scanning lines R1, R3, R5, etc., in this order. When finishing the scan with the signal light LS along the scanning line Rm (if m is an odd number; when finishing the scan along the scanning line R(m−1) if m is an even number), the main controller 211 returns the application position of the signal light LS to the scan start position RS and controls to scan with the signal light LS along the scanning lines R1, R3, R5, etc., in this order again. By executing this scan, it is possible to sequentially and repetitively acquire tomographic images along the scanning lines R1, R3, R5, etc.

The main controller 211 updates and displays the thus acquired tomographic images at a predetermined frame rate (e.g., a time interval to scan along each scanning line Ri) for each scanning line Ri (i=1, 3, 5 . . . ), thereby displaying a tomographic motion image at each scanning line Ri. Instead of thus cyclically scanning two or more cross-section positions (scanning lines), it is possible to scan two or more cross-section positions in any order and at any frequency.

The operator observes the tomographic motion image displayed on the display 240A. Then, the operator manipulates the manipulation part 240B to designate a range or timing for measurement of the tomographic still image (S9). The designation of the measurement range is performed by, for example, designating an image region in the tomographic motion image being displayed by a drag operation.

An image region to be designated is, for example, a region of interest corresponding to an attention site. On the other hand, the designation of the measurement timing is performed by for example, observing a tomographic motion image being displayed and clicking on the tomographic motion image at a desired timing. Further, in the case of designating both the measurement range and the measurement timing, it is possible to first designate the measurement range and then, at a desired timing on a certain tomographic motion image, click on the tomographic motion image.

The fundus oculi observation device 1 measures a tomographic still image corresponding to the measurement range or the measurement timing designated in step 9 (S10). In a case that the measurement range is designated, the main controller 211 controls the low-coherence light source 160 and the mirror drive mechanisms 241 and 242 to scan with the signal light LS along the cross-section position so that the measurement range is included. The CCD 184 detects the interference light LC corresponding to each scanning point where the signal light LS has been applied, and outputs a detection signal. The image forming part 220 forms a tomographic image based on the detection signal. This tomographic image includes an image in the designated measurement range. In a case that two or more cross-section positions are designated, the main controller 211 may scan these cross-section positions in any order.

Further, in the case of execution of the 3-dimensional scan, the image processor 230 forms a 3-dimensional image of the fundus oculi Ef based on a plurality of tomographic images formed by the image forming part 220.

A specific example of step 10 will be described below. In a case that the aforementioned specific example of step 8 is applied, a scan with the signal light LS is executed along, for example, each of the scanning lines R1 to Rm. In a case that the measurement range is designated, it is possible to scan only a region including the measurement range. The image forming part 220 forms tomographic images Gi (i=1 to m) along the respective scanning lines Ri. Then, the image processor 230 forms a 3-dimensional image of the fundus oculi Ef based on these tomographic images Gi.

The main controller 211 controls the display 240A to display the tomographic still image acquired in step 10 (S11). When a 3-dimensional image of the fundus oculi Ef is formed, the image processor 230 executes a rendering process to form a pseudo 3-dimensional image, and this pseudo 3-dimensional image is displayed. Moreover, when a 3-dimensional image is formed, a tomographic image at a predetermined cross-section position is displayed. This predetermined cross-section position is, for example, the aforementioned cross-section position of the tomographic motion image, a cross-section position newly designated by the operator, etc.

The operator observes the displayed tomographic still image and performs diagnosis, etc. This tomographic still image is stored in the storage 212, etc.

In step 5 in this usage pattern, it is possible to designate any number of cross-section positions. However, it is desirable that the designated number is not so large (e.g., it is desirable to be several).

This is because, for example, when a large number of cross-section positions are designated, a large number of tomographic images are displayed on the display 240A, the respective tomographic images are displayed in small size, too many tomographic images are displayed, and consequently, the observation may be difficult. Further, when a large number of cross-section positions are designated, it takes time to scan throughout all the cross-section positions with the signal light LS, and hence the frame rate of each tomographic motion image is low. As a result, it may be impossible to obtain a suitable moving image.

[Actions and Effects]

The actions and effects of the fundus oculi observation device 1 will be described below.

The fundus oculi observation device 1 acts to repetitively scan with the signal light LS along each designated cross-section position and repetitively form a tomographic image at each cross-section position, thereby displaying a tomographic motion image at each cross-section position.

Therefore, the operator can observe a tomographic motion image to designate a measurement range in a measurement object (the fundus oculi Ef). Thus, according to the fundus oculi observation device 1, it is possible to set a measurement range in a measurement object with high accuracy.

Further, the operator can observe a tomographic motion image to designate the timing for measurement of a measurement object.

Thus, according to the fundus oculi observation device 1, it is possible to acquire an image of a measurement object at a desired timing.

The fundus oculi observation device 1 is configured to, in response to designation of the measurement range and the measurement timing, scan with the signal light LS in accordance with the content of the designation and acquire a tomographic still image.

Thus, it is possible to acquire an image in the highly accurately set measurement range and also acquire an image at the desired measurement timing.

Further, according to the fundus oculi observation device 1, the number of scanning points for measuring a tomographic motion image is set so as to be smaller than the number of scanning points for measuring a tomographic still image. Therefore, it is possible to measure a tomographic still image provided for diagnosis, etc., at high resolution, and also achieve a suitable display size and a suitable frame rate for a tomographic motion image provided for preparation for the measurement. This effect will be remarkable specifically when the number of scanning lines on a tomographic motion image is set to be smaller than the number of scanning lines on a tomographic still image.

Further, according to the fundus oculi observation device 1, in response to designation of a cross-section position, etc., on a tomographic still image, a cross-section position, etc., on a tomographic motion image is set. Therefore, only by designation of a cross-section position, etc., on a tomographic still image provided for diagnosis, etc., a cross-section position, etc., on a tomographic motion image provided for designation of a measurement range, etc., is automatically set, which is convenient. The fundus oculi observation device 1 may be configured so that, for example, the automatically set cross-section position, etc., on the tomographic motion image can be changed manually.

[Other Usage Patterns]

Other usage patterns of the fundus oculi observation device 1 will be described below.

In contrast to the aforementioned usage pattern in which a cross-section position, etc., on a tomographic motion image is set in response to designation of a measurement position, etc., on a tomographic still image, it is possible to configure to execute the opposite operation. That is to say, the optical image measurement device according to the present invention can be configured to set a measurement position, etc., on a tomographic still image in response to designation of a measurement position, etc., on a tomographic motion image.

It is possible to, when the operator designates the scanning pattern (the scanning lines) on a tomographic still image, set the scanning lines for this scanning pattern as those for acquisition of a tomographic motion image. As an example, as described in the specific example of the usage pattern described above, it is possible to, when the scanning pattern on a tomographic still image is designated, set part of the scanning lines included in this scanning pattern as those for acquisition of a tomographic motion image.

As another example, it is possible to set the scanning lines included in the scanning pattern for a tomographic still image as the scanning lines for acquisition of a tomographic motion image without change. For example, it is possible to, when the cross scan is designated for acquisition of a tomographic still image, set the cross scan for acquisition of a tomographic motion image. Also in this case, it is desirable to set the number of scanning points for a tomographic motion image to be smaller than the number of scanning points for a tomographic still image.

Also in the case of designating a measurement position, etc., of a tomographic motion image, it is possible to set a measurement position, etc., of a tomographic still image in a similar manner. That is to say, it is possible to, when the operator designates the scanning pattern (the scanning lines) for a tomographic motion image, set the scanning lines for this scanning pattern as those for acquisition of a tomographic still image. As the scanning pattern for acquisition of a tomographic still image, part of the scanning lines included in the designated scanning pattern may be set, or the scanning lines included in the designated scanning pattern may be set without change.

A usage pattern with the image extracting part 231 of the fundus oculi observation device 1 will be described below (see FIG. 6). The image extracting part 231 acts to analyze a tomographic motion image and extract a region of interest as previously described.

Figure 10:
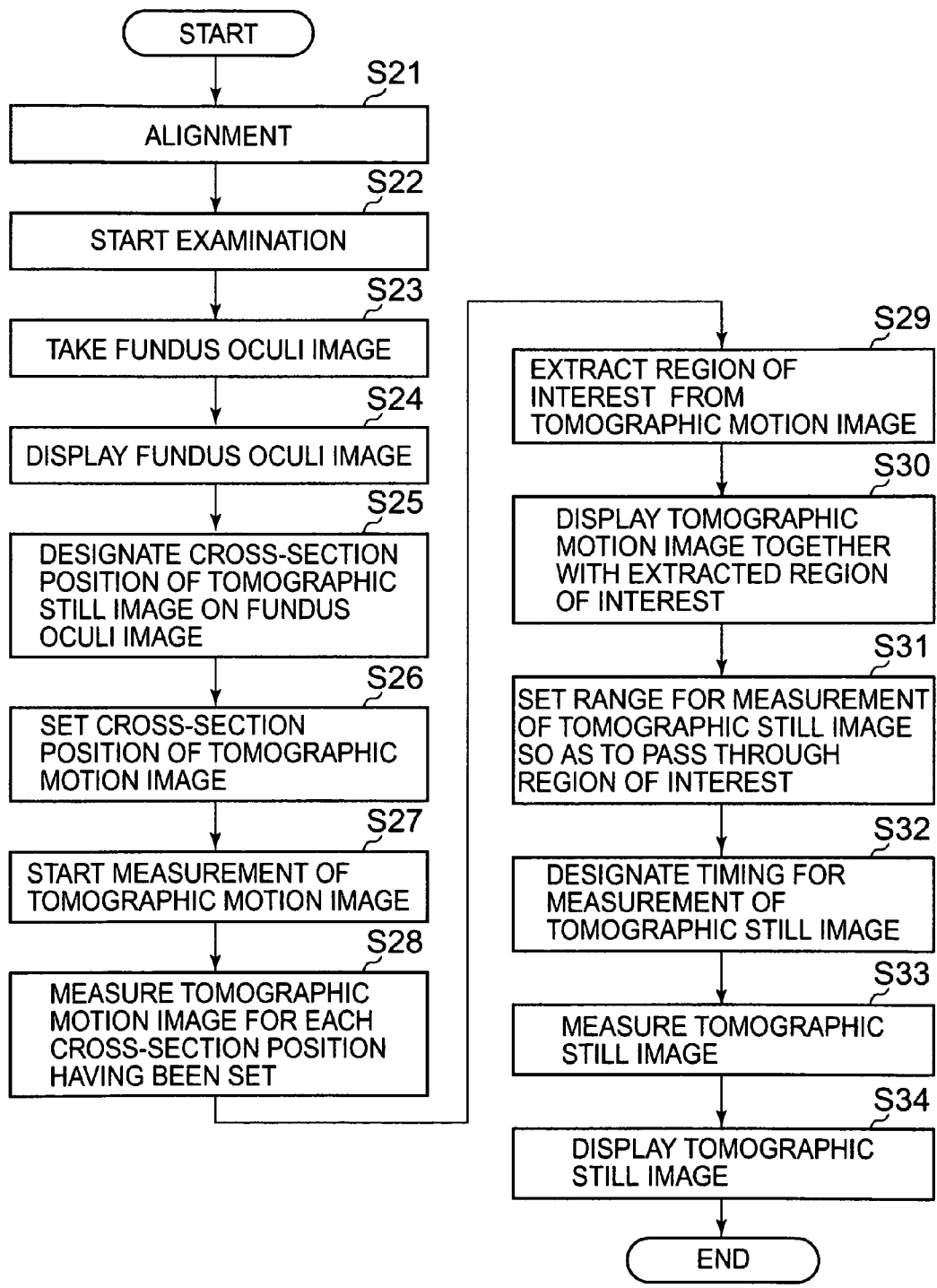
FIG. 10 is a flow chart showing an example of a usage pattern of the embodiment of the fundus oculi observation device functioning as the optical image measurement device according to the present invention.

A flow chart in FIG. 10 shows an example of this usage pattern.

First, as in the aforementioned usage pattern, when alignment is executed (S21) and start of an examination is requested (S22), the fundus oculi observation device 1 takes the fundus oculi image Ef' of the fundus oculi Ef (S23) and displays this fundus oculi image Ef' (S24).

When the operator designates a cross-section position on the displayed fundus oculi image Ef' (S25), the fundus oculi observation device 1 sets a cross-section position for acquisition of a tomographic motion image (S26). When the operator requests measurement of the tomographic motion image (S27), the fundus oculi observation device 1 measures the tomographic motion image at each cross-section position having been set (S28).

The image extracting part 231 extracts a region of interest from the acquired tomographic motion image (S29). In this case, the region of interest may be extracted from each of the frames composing the tomographic motion image, or the region of interest may be extracted from another frame by computing the correlation with a region of interest extracted from a certain frame. The region of interest may be extracted from each of the tomographic motion images, or the region of interest may be extracted only from a predetermined tomographic motion image. The predetermined tomographic motion image may be previously determined in accordance with the cross-section position, etc., or may be manually designated by the operator.

The main controller 211 displays the tomographic motion image together with the extracted region of interest on the display 240A (S30).

The scan setting part 213 sets the measurement range of the tomographic still image so as to pass through the extracted region of interest (S31). Describing more specifically, the scan setting part 213 first sets the cross-section positions (the scanning lines) for acquisition of the tomographic still image, and sets the measurement range passing through the region of interest on each of the cross-section positions. It can be determined based on the coordinate values of pixels in the region of interest whether the measurement range passes through the region of interest or not.

The operator designates a timing for measurement of the tomographic still image as needed (S32).

The fundus oculi observation device 1 measures the tomographic still image of the fundus oculi Ef based on the measurement conditions determined in steps S31 and S32 (S33) and displays the image on the display 240A (S34).

According to this usage pattern, since it is possible to extract a region of interest from a tomographic motion image and set scanning lines for acquisition of a tomographic still image so as to pass through the region of interest, it is possible to easily acquire a tomographic image or 3-dimensional image including the region of interest. Further, according to this usage pattern, since it is possible to display the extracted region of interest, the operator can observe a motion image of the region of interest. Thus, there is such a merit that it is possible to grasp the condition of the region of interest.

It is possible to inform when a region of interest is extracted from a tomographic motion image. This usage pattern is effective specifically when the region of interest is a lesion site such as a tumor. As an informing method, for example, it is possible to display a message on the display 240A. Control therefor is executed by the main controller 211. Information outputted for informing is not limited to visual information, and any information such as auditory information can be utilized.

Regarding informing that a region of interest is extracted, it is possible to configure to inform only when the extracted region of interest satisfies a predetermined condition. For example, it is possible to configure to measure the size of the extracted region of interest (such as tumor) and inform when the size is larger than a threshold.

For a follow-up, etc, it is possible to configure to previously store the sizes and positions of regions of interest extracted in the past, compare the size and position of a region of interest extracted in the current test with those extracted in the past, and inform when the size is larger or the position is different.

A usage pattern with a capture part 214 of the fundus oculi observation device 1 will be described below (see FIG. 6). While a tomographic motion image is being displayed on the display 240A, the operator manipulates the manipulation part 240B at a desired timing. In response to this manipulation, the main controller 211 controls the capture part 214, and stores the frame of the tomographic motion image displayed at the time of the manipulation into the storage 212. Such a capturing function allows the operator to closely observe a tomographic motion image and also to store a frame in an important time phase. When the resolution of a tomographic motion image is sufficient, it is possible to omit measurement of a tomographic still image.

[Modification]

The configuration described above is merely an example for favorably implementing the present invention. Therefore, it is possible to properly make any modification within the scope and intent of the present invention.

In the aforementioned embodiment, as the designating part for designating a cross-section position in an eye, the manipulation part 240B is used. That is to say, in the aforementioned embodiment, the operator manually designates a cross-section position. However, the optical image measurement device according to the present invention is not limited to the above configuration. For example, it is possible to configure to automatically designate a cross-section position by analyzing the fundus oculi image Ef to extract characteristic points (such as the central papilla, the fovea centralis, a vascular bifurcation and a lesion site) and connecting the characteristic points to designate a cross-section position. This analysis process is executed by the image processor 230.

In the aforementioned embodiment, by changing the position of the reference mirror 174, a difference in light path length between the light path of the signal light LS and the light path of the reference light LR. However, the method for changing the difference in light path is not limited to the above method. For example, by integrally moving the retinal camera unit 1A and the OCT unit 150 with respect the eye E to change the light path length of the signal light LS, it is possible to change the difference in light path length. Alternatively, by moving a measurement object in the depth direction (z-direction) it is possible to change the difference in light path length.

Although the fundus oculi observation device described in the aforementioned embodiment includes a Fourier-domain type of optical image measurement device, it is possible to apply the present invention to any optical image measurement device of a type that scans an eye with a light beam, such as the Swept Source type.

Further, although a device for acquiring an OCT image of the fundus oculi is described in the aforementioned embodiment, the configuration of the aforementioned embodiment can be applied to a device capable of acquiring an OCT image of another site in an eye, such as the cornea. Further, the present invention can be applied to an optical image measurement device that measures OCT images of various measurement objects other than an eye. For example, the optical image measurement device according to the present invention can be applied to any field, such as the optics field and the biological field.

The invention claimed is:

1. An optical image measurement device that has: an interference-light generator configured to split a low-coherence light into a signal light and a reference light and superimpose the signal light propagated through an eye and the reference light propagated through a reference object to generate an interference light; a detector configured to detect the generated interference light; and a scanner configured to scan the eye with the signal light, and that forms an image of the eye based on a detection result from the detector, the optical image measurement device comprising:

a designating part configured to designate one or more cross-section positions in the eye;

a scan setting part configured to set a number of scanning points;

a controller configured to thin out the number of scanning points set by the scan setting part to control the scanner to execute a repetitive scan with a signal light along each of the designated cross-section positions;

an image forming part configured to repetitively form a tomographic image at each of the cross-section positions, based on a detection result of an interference light based on the signal light with which the repetitive scan is executed; and a display configured to display a tomographic motion image at each of the cross-section positions, based on the repetitively formed tomographic image; and a manipulation part, wherein:

the controller is configured to, when the manipulation part is manipulated while the tomographic motion image is being displayed, control the scanner to execute a scan with a signal light along at least one cross-section position of the designated cross-section positions to scan the scanning points set by the scan setting part before being thinned out; and the image forming part is configured to form a tomographic still image at each of the at least one cross-section position, based on a detection result of an interference light based on the signal light with which the scan is executed.

2. The optical image measurement device according to claim 1, wherein the scan setting part is configured to, when two or more scanning lines with a plurality of scanning points arrayed as scanning points of the signal light are designated, set scanning lines for acquisition of the tomographic motion image based on the two or more scanning lines.

3. The optical image measurement device according to claim 2, wherein the scan setting part is configured to set two or more scanning lines acquired by removing one or more scanning points from the two or more scanning lines, as scanning lines for acquisition of the tomographic motion image.

4. The optical image measurement device according to claim 2, wherein the scan setting part is configured to set part of the two or more scanning lines as scanning lines for acquisition of the tomographic motion image.

5. The optical image measurement device according to claim 1, wherein the scan setting part is configured to, when scanning points of a signal light for acquisition of the tomographic motion image are designated before measurement for acquisition of the tomographic still image, set a larger number of scanning points than the designated scanning points, as scanning points for acquisition of the tomographic still image.

6. The optical image measurement device according to claim 1, further comprising an extracting part configured to analyze the tomographic motion image to extract a predetermined region of interest, wherein the scan setting part is configured to set scanning lines of a signal light for acquisition of the tomographic still image so that a signal light is propagated through an attention site in the eye corresponding to the extracted region of interest.

7. The optical image measurement device according to claim 1, further comprising an extracting part configured to analyze the tomographic motion image and extract a predetermined region of interest, wherein the display is configured to display the extracted region of interest.

8. The optical image measurement device according to claim 1, further comprising:

an extracting part configured to analyze the tomographic motion image to extract a predetermined region of interest; and an informing part configured to inform when the region of interest is extracted.

9. The optical image measurement device according to claim 1, further comprising a recording part configured to selectively record a frame of a tomographic motion image displayed on the display.

10. The optical image measurement device according to claim 1, wherein the designating part includes an imaging part configured to take an image of the eye, and a designation manipulation part configured to designate a cross-section position on the taken image displayed on the display.

* * * * *